United States Patent
Zhang et al.

(10) Patent No.: US 9,093,722 B2
(45) Date of Patent: Jul. 28, 2015

(54) FUNCTIONALIZED IONIC LIQUID ELECTROLYTES FOR LITHIUM ION BATTERIES

(75) Inventors: Zhengcheng Zhang, Naperville, IL (US); Wei Weng, Argonne, IL (US); Lu Zhang, Naperville, IL (US); Khalil Amine, Oakbrook, IL (US)

(73) Assignee: UCHICAGO ARGONNE, LLC, Chicago, IL (US)

( * ) Notice: Subject to any disclaimer, the term of this patent is extended or adjusted under 35 U.S.C. 154(b) by 715 days.

(21) Appl. No.: 12/895,395

(22) Filed: Sep. 30, 2010

(65) Prior Publication Data
US 2012/0082903 A1 Apr. 5, 2012

(51) Int. Cl.
| | |
|---|---|
| H01M 10/39 | (2006.01) |
| C07D 233/60 | (2006.01) |
| C07F 5/04 | (2006.01) |
| C07F 7/08 | (2006.01) |
| C07F 9/54 | (2006.01) |
| C07F 9/655 | (2006.01) |
| H01M 10/052 | (2010.01) |
| H01M 10/0568 | (2010.01) |
| H01M 10/0569 | (2010.01) |

(52) U.S. Cl.
CPC ........... *H01M 10/399* (2013.01); *C07D 233/60* (2013.01); *C07F 5/04* (2013.01); *C07F 7/0854* (2013.01); *C07F 9/5407* (2013.01); *C07F 9/5414* (2013.01); *C07F 9/65515* (2013.01); *H01M 10/052* (2013.01); *H01M 10/0568* (2013.01); *H01M 10/0569* (2013.01); *H01M 2300/0045* (2013.01); *Y02E 60/122* (2013.01)

(58) Field of Classification Search
CPC ..................... H01M 10/0569; H01M 10/0568; H01M 10/052; H01M 10/399; H01M 2300/0045; Y02E 60/122
USPC .......... 429/328, 329, 200, 322, 323; 548/110; 556/405
See application file for complete search history.

(56) References Cited

U.S. PATENT DOCUMENTS

| | | | |
|---|---|---|---|
| 4,550,064 A | 10/1985 | Yen et al. | |
| 5,487,959 A | 1/1996 | Koksbang | |
| 5,510,209 A | 4/1996 | Abraham et al. | |
| 5,833,854 A | 11/1998 | Zwijnenburg et al. | |
| 6,177,414 B1 | 1/2001 | Tomalia et al. | |
| 6,245,465 B1 | 6/2001 | Angell et al. | |
| 6,312,809 B1 | 11/2001 | Crooks et al. | |
| 6,787,268 B2 | 9/2004 | Koike et al. | |
| 6,841,303 B2 | 1/2005 | Park et al. | |
| 7,268,238 B2 | 9/2007 | Woo et al. | |
| 7,344,804 B2 | 3/2008 | Klaassen | |
| 2001/0033964 A1 | 10/2001 | Heider et al. | |
| 2001/0033974 A1 | 10/2001 | Gavelin et al. | |
| 2002/0177039 A1* | 11/2002 | Lu et al. | ......... 429/213 |
| 2003/0050433 A1 | 3/2003 | Agarwal et al. | |
| 2003/0157409 A1 | 8/2003 | Huang | |
| 2004/0151951 A1 | 8/2004 | Hyung et al. | |
| 2004/0157126 A1 | 8/2004 | Belharouak et al. | |
| 2005/0196676 A1 | 9/2005 | Singh et al. | |
| 2007/0141461 A1 | 6/2007 | Lin et al. | |
| 2007/0298326 A1 | 12/2007 | Angell et al. | |
| 2008/0145763 A1 | 6/2008 | Koh et al. | |
| 2008/0193855 A1 | 8/2008 | McDonald | |
| 2009/0086408 A1 | 4/2009 | Koh et al. | |
| 2009/0088583 A1* | 4/2009 | West et al. | ..................... 556/413 |

FOREIGN PATENT DOCUMENTS

| | | | |
|---|---|---|---|
| DE | 1231701 | * | 1/1967 |
| EP | 0 477 541 B1 | | 4/1992 |

OTHER PUBLICATIONS

Niedermeyer et al. "Understanding siloxane functionalised ionic liquids", Phys. Chem. Chem. Phys., 2010 (published on the web Jan. 27, 2010), 12(8), pp. 2018-2029.*

(Continued)

*Primary Examiner* — Laura Weiner
(74) *Attorney, Agent, or Firm* — Foley & Lardner LLP

(57) ABSTRACT

An ionic liquid that is a salt has a Formula:

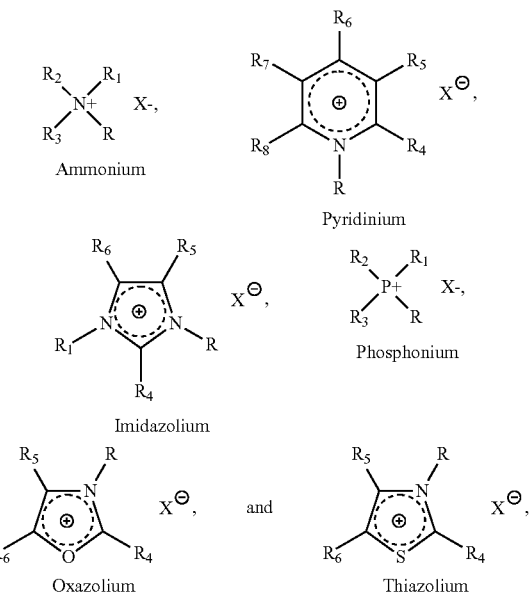

Such ionic liquids may be used in electrolytes and in electrochemical cells.

20 Claims, 8 Drawing Sheets

(56) References Cited

OTHER PUBLICATIONS

U.S. Appl. No. 12/146,020, filed Jun. 25, 2008.

Abraham, K.M. et al., "A Polymer Electrolyte-Based Rechargeable Lithium/Oxygen Battery," Journal of Electrochemical Society, vol. 143, No. 1, 1996, pp. 1-5.

Amine, K. et al., "Hybrid Electrolyte for Electrochemical Cells", Electrochemical Energy Storage Theme, CSE Division, Jun. 17, 2009, 11 pps.

Amine, K. et al., "Novel silane compounds as electrolyte solvents for Li-ion batteries", Electrochemistry Communications, 8, 2006, pp. 429-433.

Hammond, P., "1997 Progress Report: Design and Synthesis of Dendrimer Block Copolymers as Nanoporous Membranes for Environmental Separation Applications," National Center for Environmental Research, U.S. EPA, 1997, 4 pps.

Huggins, R.A., "Transient behavior of insertion reaction electrodes", Solid State Ionics, 86-88, 1996, pp. 41-48.

Lu, Z. et al., "Can All the Lithium be Removed from T2-$Li_{2/3}$[$Ni_{1/3}Mn_{2/3}$]$O_2$?", Journal of The Electrochemical Society, 148, No. 7, 2001, pp. A710-A715.

McMillian, R. et al., "Fluoroethylene carbonate electrolyte and its use in lithium ion batteries with graphite anodes", Journal of Power Sources, 81-82, 1999, pp. 20-26.

Rikukawa, M. et al., "Proton-conducting polymer electrolyte membranes based on hydrocarbon polymers," Progress in Polymer Sciences, vol. 25, 2000, pp. 1463-1502, published by Elsevier Science Ltd.

Schlüter, A. et al., "Dendronized Polymers: Synthesis, Characterization, Assembly at Interfaces, and Manipulation," Angew. Chem. Int. Ed., vol. 39, 2000, pp. 865-883, published by Wiley-VCH Verlag GmbH.

Seel, J.A. et al., "Electrochemical Intercalation of $PF_6$ into Graphite", Journal of The Electrochemical Society, 147, No. 3, 2000, pp. 892-898.

Sun, X. et al., "Doped sulfone electrolytes for high voltage Li-ion cell applications", Electrochemistry Communications, 11, 2009, pp. 1418-1421.

Sun, X. et al., "New sulfone electrolytes for rechargeable lithium batteries. Part I. Oligoether-containing sulfones", Electrochemistry Communications, 7, 2005, pp. 261-266.

Sun, X. et al., "New sulfone electroytes Part II. Cyclo alkyl group containing sulfones", Solid State Ionics, 175, 2004, pp. 257-260.

Xu, K. et al., "High Anodic Stability of a New Electrolyte Solvent: Unsymmetric Noncyclic Aliphatic Sulfone", Journal of The Electrochemical Society, 145, No. 4, 1998, pp. L70-L72.

Xu, K. et al., "Sulfone-Based Electrolytes for Lithium-Ion Batteries", Journal of The Electrochemical Society, 149, 7, 2002, pp. A920-A926.

Zhang, Z. et al., "Functional Ionic Liquids as Electrolytes for Lithium-ion Battery", Argonne National Laboratory IPDG Meeting, May 17, 2010, 22 pps.

\* cited by examiner

FUNCTIONALIZED IONIC LIQUID ELECTROLYTES FOR LITHIUM ION BATTERIES

STATEMENT OF GOVERNMENT RIGHTS

The United States Government has rights in this invention pursuant to Contract No. DE-AC02-06CH11357 between the United States Government and UChicago Argonne, LLC, representing Argonne National Laboratory.

TECHNICAL FIELD

The present technology relates to ionic liquids, including room temperature ionic liquids, that may be used in electrolytes, electrolytic solutions and electrochemical devices. More particularly, the present technology relates to functionalized ionic liquids which are usable as electrolytes for lithium ion batteries having a high ionic conductivity, good solid electrolyte interphase (SEI) formation, high wettability, and high voltage stability.

BACKGROUND

Ionic liquids are substances, which are made up only from ions and have a melting point of <100° C. or are, ideally, liquid at ambient temperature. They have been proposed for use in electrolytes for lithium and lithium-ion batteries, as they exhibit relatively favorable electrochemical stability and high ionic conductivity. Despite the potential advantages, ionic liquids have not been widely used as electrolytes for lithium and lithium ion batteries due to a number of significant disadvantages. Although lithium-ion cells using $LiMnO_2$ and $Li_4Ti_5O_{12}$ as electrode materials show satisfactory cycling behavior using ionic liquid as electrolyte solvent, this cell configuration suffers from the relatively small voltage of 2.5 V. In addition, the cell has low rate capability due to the high viscosity and poor wettability of the ionic liquid with electrode materials.

Moreover, early experiments to cycle lithium-ion batteries using carbonaceous negative electrode materials and ionic liquid-based electrolytes failed. Any ionic liquid sample tested was reduced at the low potential at which the intercalation of lithium into the graphite proceeds. It is believed that the reduction of the ionic liquids proceeds due to the formation of dimeric species. For commercial applications, lithium metal is, however, not advantageous. Due to the high reactivity of its surface, lithium is potentially hazardous, especially at elevated temperatures. Proposals to stabilize lithiated graphite electrodes for use in lithium-ion batteries include admixture of small amounts of highly active film forming additives. Such additives could protect against the continued reduction of the electrolyte itself at the surface of the low potential graphite. However, in most cases, the additives have issues associated with the poor solubility in ionic liquid electrolytes.

SUMMARY

The present technology provides new ionic liquids for use in electrolytes and electrochemical devices such as capacitors and lithium ion batteries. The ionic liquids bear functional groups so that should allow the ionic liquid itself to form passivation films on the surface of graphite-based anode materials and ensure stable cycling performance. The new ionic liquids also decrease the viscosity of the electrolytes compared to conventional ionic liquids, increasing their ionic conductivity; provide good electrode wettability by introducing surfactant groups; and tolerate high potential, which reduces problems related to the use of 4.8V transition metal oxides, especially against overcharge. Finally, the ionic liquids of the present technology may also exhibit one or more of reduced flammability, thereby reducing the risk of burning and explosion in a misused battery; reduced vapor pressure, even at elevated temperatures; and are not environmentally hazardous.

BRIEF DESCRIPTION OF THE DRAWINGS

FIG. 1A) and triethyl-(methylenepentamethyldisiloxane) phosphonium bis (trifluoromethylsulfonyl)imide (IL1-TFSI, FIG. 1B).

DETAILED DESCRIPTION

Figure 1A:
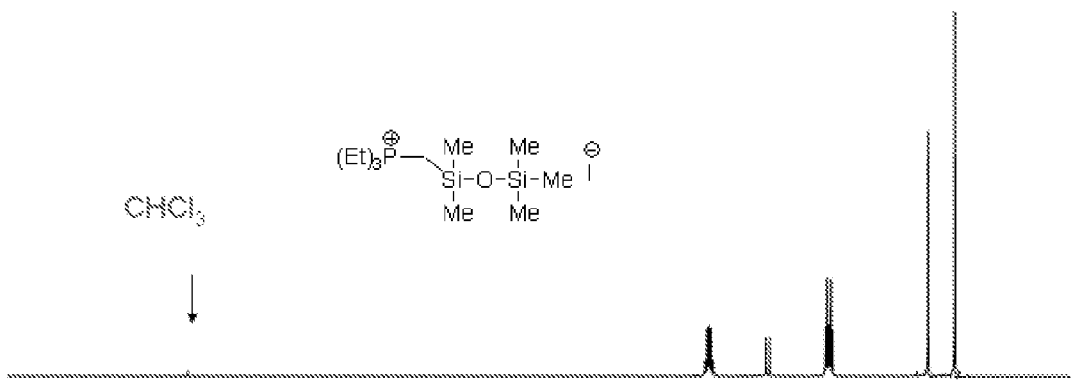
FIGS. 1A and 1B. $^1$H-NMR of triethyl-(methylenepentamethyldisiloxane) phosphonium iodide (ILM.

The following terms are used throughout as described below, unless context clearly indicates otherwise.

Alkyl groups include straight chain and branched chain saturated hydrocarbon groups having from 1 to 14 carbons unless indicated otherwise. For example, a $C_{1-6}$ alkyl group includes alkyl groups with 1, 2, 3, 4, 5, or 6 carbon atoms. In some embodiments, an alkyl group has from 1 to 12 carbon atoms, from to 10 carbons, from 1 to 8, 1 to 6, or 1, 2, 3 or 4 carbon atoms. Examples of straight chain alkyl groups include groups such as methyl, ethyl, n-propyl, n-butyl, n-pentyl, n-hexyl, n-heptyl, and n-octyl, n-decyl, n-dodecyl and n-tetradecyl groups. Examples of branched chain alkyl groups include, but are not limited to, isopropyl, iso-butyl, sec-butyl, tert-butyl, neopentyl, isopentyl, and 2,2-dimethylpropyl groups. Alkyl groups may be unsubstituted or are optionally substituted with one or more hydroxyl or halogen groups.

Cycloalkyl groups include mono-, bi- or tricyclic alkyl groups having from 3 to 12 carbon atoms in the ring(s), or, in some embodiments, 3 to 10, 3 to 8, or 3, 4, 5, or 6 carbon atoms. Exemplary monocyclic cycloalkyl groups include, but are not limited to, cyclopropyl, cyclobutyl, cyclopentyl, cyclohexyl, cycloheptyl, and cyclooctyl groups. In some embodiments, the cycloalkyl group has 3 to 8 ring members, whereas in other embodiments the number of ring carbon atoms range from 3 to 5, 3 to 6, or 3 to 7. Bi- and tricyclic ring systems include both bridged cycloalkyl groups and fused rings, such as, but not limited to, adamantyl, decalinyl, and the like. Cycloalkyl groups may be unsubstituted or substituted as alkyl groups are.

Haloalkyl groups include alkyl groups as defined above in which 1 or more of the hydrogen atoms are replaced by a halogen (i.e., F, Cl, Br, or I). In some embodiments the haloalkyl group bears from 1 to 3 halogens. In others, the haloalkyl is perhalogenated such as perfluorinated or perchlorinated. Examples of haloalkyl groups include but are not limited to —$CH_2Cl$, —$CH_2F$, —$CF_3$, —$CH_2CH_2Br$, and —$CH_2CF_3$.

Hydroxyalkyl groups are alkyl groups which bear at least one hydroxyl group, i.e., OH. In some embodiments the hydroxyalkyl group bears 1 or 2 hydroxyl groups.

Alkylene groups are alkyl groups, as defined herein, which are divalent; i.e., they have two points of attachment to a compound of the present technology.

Aryl groups are cyclic aromatic hydrocarbons containing 6-14 carbon atoms and do not contain heteroatoms. Aryl groups herein include monocyclic, bicyclic and tricyclic ring systems, including fused rings. Thus, aryl groups include, but are not limited to, phenyl, azulenyl, heptalenyl, biphenyl, fluorenyl, phenanthrenyl, anthracenyl, indenyl, indanyl, pentalenyl, and naphthyl groups. In some embodiments, aryl groups contain from 6-12 or even 6-10 carbon atoms in the ring portions of the groups. In some embodiments, the aryl groups are phenyl or naphthyl. Aryl groups may also include fused aromatic-aliphatic ring systems, e.g., indanyl, tetrahydronaphthyl, and the like. Aryl groups may be unsubstituted or optionally substituted with one or more alkyl, halo groups or one or more halogens. In some embodiments the aryl groups are substituted with 1, 2 or 3 alkyl groups and/or 1-5 halogens.

Aralkyl groups are alkyl groups as defined above in which a hydrogen or carbon bond of an alkyl group is replaced with a bond to an aryl group as defined above. In some embodiments, aralkyl groups contain 7 to 16 carbon atoms, 7 to 14 carbon atoms, or 7 to 10 carbon atoms. Substituted aralkyl groups may be substituted at the alkyl, the aryl or both the alkyl and aryl portions of the group. Representative aralkyl groups include but are not limited to benzyl and phenethyl groups and fused (cycloalkylaryl)alkyl groups such as 4-indanylethyl. Aralkyl groups may be unsubstituted or substituted. Representative substituted aralkyl groups may be substituted one or more times with alkyl groups or halogens as for aryl and alkyl groups.

Heteroaryl groups are aromatic ring compounds containing 5 or more ring members, of which one or more is a heteroatom selected from N, O, S and P. Heteroaryl groups include, but are not limited to, groups such as pyrrolyl, pyrazolyl, triazolyl, tetrazolyl, oxazolyl, isoxazolyl, thiazolyl, pyridinyl, pyridazinyl, pyrimidinyl, pyrazinyl, thiophenyl, benzothiophenyl, furanyl, benzofuranyl, indolyl, azaindolyl (pyrrolopyridinyl), indazolyl, benzimidazolyl, imidazopyridinyl (azabenzimidazolyl), pyrazolopyridinyl, triazolopyridinyl, benzotriazolyl, benzoxazolyl, benzothiazolyl, benzothiadiazolyl, imidazopyridinyl, isoxazolopyridinyl, thianaphthyl, purinyl, xanthinyl, adeninyl, guaninyl, quinolinyl, isoquinolinyl, tetrahydroquinolinyl, quinoxalinyl, and quinazolinyl groups. Heteroaryl groups include fused ring compounds in which all rings are aromatic such as indolyl groups and include fused ring compounds in which only one of the rings is aromatic, such as 2,3-dihydro indolyl groups. Heteroaryl groups may be unsubstituted or optionally substituted with one or more alky groups or one or more halogens. In some embodiments the aryl groups are substituted with 1, 2 or 3 alkyl groups and/or 1-5 halogens.

Heteroarylalkyl groups are alkyl groups as defined above in which a hydrogen or carbon bond of an alkyl group is replaced with a bond to a heteroaryl group as defined above. Representative heteroarylalkyl groups include, but are not limited to, furan-2-yl-methyl, imidazol-4-yl-methyl, pyridin-3-yl-methyl, and indol-2-yl-propyl. In some embodiments, the alkyl portion of the heteroarylalkyl group has from 1 to 6 carbon atoms (i.e., 1, 2, 3, 4, 5, or 6). Heteroarylalkyl groups may be unsubstituted or substituted as heteroaryl and alkyl groups are.

A $C_{3-5}$ cyclic carbonate has from 3 to 5 carbon atoms in the ring, providing a 5 to 7 membered carbonate ring. Thus, for example, a $C_{3-5}$ cyclic carbonate includes any of the following structures:

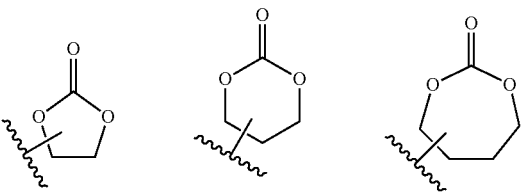

Aluminate is an aluminum oxide anion such as, but not limited to $[Al_xO_y]^-$.

A halogen refers to any of fluorine, chlorine, bromine or iodine atoms. A halide is a halogen anion such as $F^-$, $Cl^-$, $Br^-$ or $F^-$.

An isocyanate group has the chemical formula —N═C═O.

A maleic anhydride group (cis-butenedioic anhydride) has the structure shown below and may be attached to a compound at carbons 4 or 5.

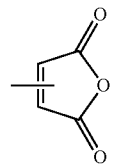

An oxalic borate group is a boron anion to which one or two oxalate groups are bound. Oxalic borates thus include but are not limited to $[B(C_2O_4)_2]^-$ and $[F_2B(C_2O_4)]^-$. As part of a compound of formula I, the oxalic borate has a single oxalate group and may have a formula such as —$[B(F)(C_2O_4)]^-$.

A succinic anhydride group has the structure shown below and may be attached to a compound at carbons 4 or 5.

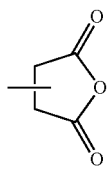

A sulfate group has the chemical formula $SO_4^{2-}$. Hence, alkyl sulfates and aryl sulfates employed in the present technology are sulfate monoesters of alkyl and aryl groups as defined herein. Thus alkyl and aryl sulfates include but are not limited to octyl sulfate, dodecyl sulfate and the like.

Sulfolane is 2,3,4,5-tetrahydrothiophene-1,1-dioxide and may be attached to a compound at any of carbons 2, 3, 4, or 5.

A sulfonate group has the chemical formula $—SO_3^-$. Thus, alkyl sulfonates are alkyl groups as defined herein bearing a sulfonate group, e.g., methyl sulfonate, ethyl sulfonate, dodecyl sulfonate and the like. Fluoroalkyl sulfonates are alkyl groups which bear 1 or more fluorine atoms and a sulfonate group. Fluoroalkyl sulfonates include trifluoromethane sulfonate, perfluoroethyl sulfonate and the like. Likewise, an aryl sulfonate is an aryl group as defined herein which bears a sulfonate group and optionally, one or more alkyl groups. Aryl sulfonates thus include for example, benzene sulfonate, naphthalene sulfonate, dodecylbenzene sulfonate and cumene sulfonate.

A sulfone group has the chemical formula $—S(O)_2R^a$ wherein $R^a$ is a $C_{1-6}$ alkyl group. In some embodiments, $R^a$ is a $C_{2-4}$ alkyl group In one aspect, the present technology provides ionic liquids that bear passivating functional groups. The functional groups allow the ionic liquid to passivate the surface of, e.g., carbon-based electrodes in an electrochemical device during operation of the device. These new ionic liquids include a salt having a Formula selected from the group consisting of:

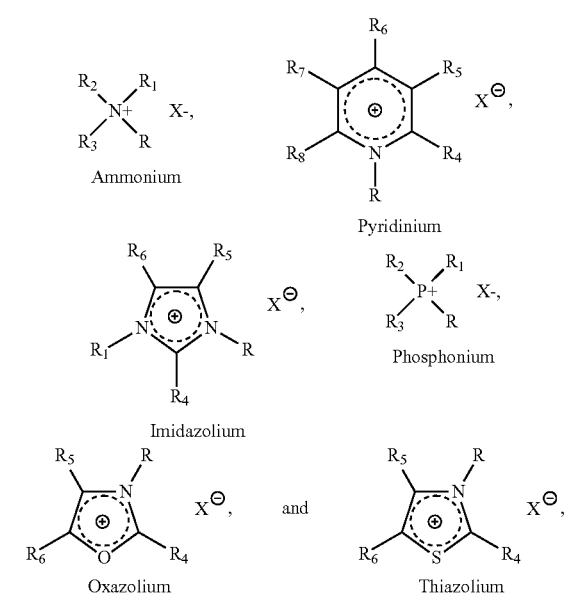

wherein R is selected from the group consisting of —$CH_2Si(R'')_2[OSi(R'')_2]_mOSi(R'')_3$, (R')—$(OCH_2CH_2)_n$—(OR''), a $C_{3-5}$ cyclic carbonate, an oxalic borate group, a maleic anhydride group, a succinic anhydride group, a sulfolane, and a $C_{1-6}$ alkyl group substituted with a substituent selected from an isocyanate, sulfone, sulfolane, —$OCO_2R''$, $C_{3-5}$ cyclic carbonate, or oxalic borate group;

R' is a $C_{1-4}$ alkylene group;

R'' is an alkyl group;

$R_1$, $R_2$, and $R_3$ are independently at each occurrence an alkyl, haloalkyl, alkyl substituted with carboxylate, aminoalkyl, cycloalkyl, aryl, heteroaryl, aralkyl, or heteroaralkyl group; or two of $R_1$, $R_2$, and $R_3$ join together to form a $C_{4-5}$ alkylene group;

$R_4$, $R_5$, $R_6$, $R_7$, and $R_8$ are independently at each occurrence H or an alkyl, haloalkyl, hydroxyalkyl, cycloalkyl, aryl, heteroaryl, aralkyl, or heteroaralkyl group;

$X^-$ is an anion selected from the group consisting of boron tetrafluoride, aluminate, (oxalate)borate, difluoro(oxalate)borate, phosphorus hexafluoride, alkylsulfonate, fluoroalkylsulfonate, arylsulfonate, bis(alkylsulfonyl)amide, perchlorate, bis(fluoroalkylsulfonyl)amide, bis(arylsulfonyl)amide, alkyl fluorophosphate, (fluoroalkylsulfonyl)(fluoroalkylcarbonyl)amide, halide, nitrate, nitrite, sulfate, hydrogen sulfate, alkyl sulfate, aryl sulfate, carbonate, bicarbonate, carboxylate, phosphate, hydrogen phosphate, dihydrogen phosphate, hypochlorite, an anionic site of a cation-exchange resin, and a mixture of any two or more thereof;

n is an integer from 1 to 4; and m is an integer from 0 to 10.

It will be understood that each dashed circle and plus sign in the chemical formulas represent a cationic aromatic system.

In some embodiments of the ionic liquid, the salt has the Formula selected from the group consisting of:

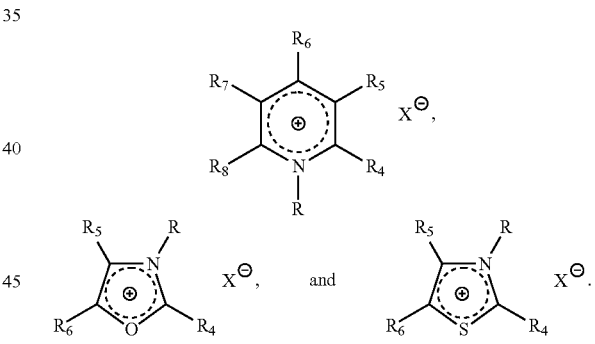

In other embodiments, the salt has the Formula selected from the group consisting of:

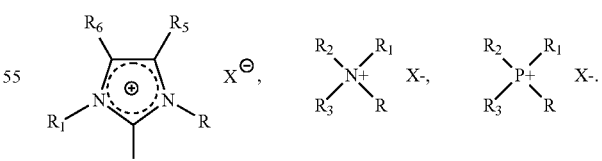

In some embodiments of the ionic liquid, R is selected from the group consisting of —(R')—$(OCH_2CH_2)_n$—(OR''), —$CH_2Si(R'')_2[OSi(R'')_2]_mOSi(R'')_3$, and a $C_{1-6}$ alkyl group substituted with a sulfone group. For example R may be —$(CH_2)$—$(OCH_2CH_2)_n$—$(OCH_3)$, —$CH_2Si(CH_3)_2$—$[OSi(CH_3)_2]_mOSi(CH_3)_3$, or —$(CH_2)_nSO_2CH_3$. In some embodiments, R'' is a $C_{1-4}$ alkyl group.

In some embodiments of the ionic liquid, $R_1$, $R_2$, and $R_3$ are independently at each occurrence selected from the group consisting of a $C_{1-6}$ alkyl, hydroxyalkyl, and a haloalkyl group.

In some embodiments, $R_4$, $R_5$, $R_6$, $R_7$, and $R_8$ are independently at each occurrence a hydrogen or a $C_{1-6}$ alkyl group. In certain embodiments, $R_4$, $R_5$, and $R_6$ are each H.

In some embodiments the counterion, $X^-$, of the ionic liquid is $[CF_3CO_2]^-$; $[C_2F_5CO_2]^-$; $[ClO_4]^-$; $[BF_4]^-$; $[AsF_6]^-$; $[PF_6]^-$; $[PF_2(C_2O_4)_2]^-$; $[PF_4C_2O_4]^-$; $[CF_3SO_3]^-$; $[N(CF_3SO_2)_2]^-$; $[C(CF_3SO_2)_3]^-$; $[N(SO_2C_2F_5)_2]^-$; alkyl fluorophosphate; $[B(C_2O_4)_2]^-$; $[BF_2C_2O_4]^-$; $[B_{12}Y_{12-k}H_k]^{2-}$; $[B_{10}Y_{10-k'}H_{k'}]^{2-}$; or a mixture of any two or more thereof, wherein Y is a halogen, k is an integer from 0 to 12 and k' is an integer from 1 to 10.

In some embodiments, the ionic liquid is a room temperature ionic liquid.

Exemplary ionic liquids include but are not limited to imidazolium salts with oligo(ethylene glycol) groups such as:
1-ethyl-3-((2-methoxyethoxy)methyl)-1H-imidazol-3-ium bis(trifluoromethanesulfonyl)imide,
1-ethyl-3-((2-(2-methoxyethoxy)ethoxy)methyl)-1H-imidazol-3-ium bis(trifluoromethanesulfonyl)imide,
3-2,5,8,11-tetraoxadodecyl-1-ethyl-1H-imidazol-3-ium bis(trifluoromethanesulfonyl)imide,
1-ethyl-3-((2-methoxyethoxy)methyl)-1H-imidazol-3-ium bis(fluoromethanesulfonyl)imide,
1-ethyl-3-((2-(2-methoxyethoxy)ethoxy)methyl)-1H-imidazol-3-ium bis(fluoromethanesulfonyl)imide,
3-2,5,8,11-tetraoxadodecyl-1-ethyl-1H-imidazol-3-ium bis(fluoromethanesulfonyl)imide;
1-ethyl-3-((2-methoxyethoxy)methyl)-1H-imidazol-3-ium bis(oxalato)borate,
1-ethyl-3-((2-(2-methoxyethoxy)ethoxy)methyl)-1H-imidazol-3-ium bis(oxalato)borate,
3-2,5,8,11-tetraoxadodecyl-1-ethyl-1H-imidazol-3-ium bis(oxalato)borate;
1-ethyl-3-((2-methoxyethoxy)methyl)-1H-imidazol-3-ium hexafluorophosphate,
1-ethyl-3-((2-(2-methoxyethoxy)ethoxy)methyl)-1H-imidazol-3-ium hexafluorophosphate, and
3-2,5,8,11-tetraoxadodecyl-1-ethyl-1H-imidazol-3-ium hexafluorophosphate.

Further exemplary ionic liquids include but are not limited to imidazolium salts with siloxane groups such as:
1-ethyl-3-(methylenepentamethyldisiloxane)-1H-imidazol-3-ium bis(trifluoromethanesulfonyl)imide,
1-ethyl-3-(methyleneheptamethyltrisiloxane)-1H-imidazol-3-ium bis(trifluoromethanesulfonyl)imide,
1-ethyl-3-(methyleneoctamethyltetrasiloxane)-1H-imidazol-3-ium bis(trifluoromethanesulfonyl)imide,
1-ethyl-3-(methylenepentamethyldisiloxane)-1H-imidazol-3-ium bis(oxalato)borate,
1-ethyl-3-(methyleneheptamethyltrisiloxane)-1H-imidazol-3-ium bis(oxalato)borate,
1-ethyl-3-(methyleneoctamethyltetrasiloxane)-1H-imidazol-3-ium bis(oxalato)borate,
1-ethyl-3-(methylenepentamethyldisiloxane)-1H-imidazol-3-ium bis(fluoromethanesulfonyl)imide,
1-ethyl-3-(methyleneheptamethyltrisiloxane)-1H-imidazol-3-ium bis(fluoromethanesulfonyl)imide,
1-ethyl-3-(methyleneoctamethyltetrasiloxane)-1H-imidazol-3-ium bis(fluoromethanesulfonyl)imide;
1-ethyl-3-(methylenepentamethyldisiloxane)-1H-imidazol-3-ium hexafluorophosphate,
1-ethyl-3-(methyleneheptamethyltrisiloxane)-1H-imidazol-3-ium hexafluorophosphate, and
1-ethyl-3-(methyleneoctamethyltetrasiloxane)-1H-imidazol-3-ium hexafluorophosphate.

Exemplary ionic liquids include but are not limited to imidazolium salts with sulfone groups such as:
1-ethyl-3-(2-(methylsulfonyl)ethyl)-1H-imidazol-3-ium bis(trifluoromethanesulfonyl)imide,
1-ethyl-3-(2-(ethylsulfonyl)ethyl)-1H-imidazol-3-ium bis(trifluoromethanesulfonyl)imide,
1-ethyl-3-(2-(propylsulfonyl)ethyl)-1H-imidazol-3-ium bis(trifluoromethanesulfonyl)imide,
1-ethyl-3-(2-(butylsulfonyl)ethyl)-1H-imidazol-3-ium bis(trifluoromethanesulfonyl)imide,
1-ethyl-3-(2-(methylsulfonyl)ethyl)-1H-imidazol-3-ium bis(oxalato)borate,
1-ethyl-3-(2-(ethylsulfonyl)ethyl)-1H-imidazol-3-ium bis(oxalato)borate,
1-ethyl-3-(2-(propylsulfonyl)ethyl)-1H-imidazol-3-ium bis(oxalato)borate,
1-ethyl-3-(2-(butylsulfonyl)ethyl)-1H-imidazol-3-ium bis(oxalato)borate,
1-ethyl-3-(2-(methylsulfonyl)ethyl)-1H-imidazol-3-ium bis(fluoromethanesulfonyl)imide,
1-ethyl-3-(2-(ethylsulfonyl)ethyl)-1H-imidazol-3-ium bis(fluoromethanesulfonyl)imide,
1-ethyl-3-(2-(propylsulfonyl)ethyl)-1H-imidazol-3-ium bis(fluoromethanesulfonyl)imide;
1-ethyl-3-(2-(butylsulfonyl)ethyl)-1H-imidazol-3-ium bis(fluoromethanesulfonyl)imide;
1-ethyl-3-(2-(methylsulfonyl)ethyl)-1H-imidazol-3-ium hexafluorophosphate,
1-ethyl-3-(2-(ethylsulfonyl)ethyl)-1H-imidazol-3-ium hexafluorophosphate,
1-ethyl-3-(2-(propylsulfonyl)ethyl)-1H-imidazol-3-ium hexafluorophosphate, and
1-ethyl-3(2-(butylsulfonyl)ethyl)-1H-imidazol-3-ium hexafluorophosphate.

Exemplary ionic liquids include but are not limited to imidazolium salts with carbonate groups such as:
1-ethyl-3-((2-oxo-1,3-dioxolan-4-yl)methyl)-1H-imidazol-3-ium bis(trifluoromethanesulfonyl)imide,
1-ethyl-3-((2-oxo-1,3-dioxolan-4-yl)ethyl)-1H-imidazol-3-ium bis(trifluoromethanesulfonyl)imide,
1-ethyl-3-((2-oxo-1,3-dioxolan-4-yl)propyl)-1H-imidazol-3-ium bis(trifluoromethanesulfonyl)imide,
1-ethyl-3-((2-oxo-1,3-dioxolan-4-yl)methyl)-1H-imidazol-3-ium bis(oxalato)borate,
1-ethyl-3-((2-oxo-1,3-dioxolan-4-yl)ethyl)-1H-imidazol-3-ium bis(oxalato)borate,
1-ethyl-3-((2-oxo-1,3-dioxolan-4-yl)propyl)-1H-imidazol-3-ium bis(oxalato)borate,
1-ethyl-3-((2-oxo-1,3-dioxolan-4-yl)methyl)-1H-imidazol-3-ium bis(fluoromethanesulfonyl)imide,
1-ethyl-3-((2-oxo-1,3-dioxolan-4-yl)ethyl)-1H-imidazol-3-ium bis(fluoromethanesulfonyl)imide,
1-ethyl-3-((2-oxo-1,3-dioxolan-4-yl)propyl)-1H-imidazol-3-ium bis(fluoromethanesulfonyl)imide;
1-ethyl-3-((2-oxo-1,3-dioxolan-4-yl)methyl)-1H-imidazol-3-ium hexafluorophosphate,
1-ethyl-3-((2-oxo-1,3-dioxolan-4-yl)ethyl)-1H-imidazol-3-ium hexafluorophosphate, and
1-ethyl-3-((2-oxo-1,3-dioxolan-4-yl)propyl)-1H-imidazol-3-ium hexafluorophosphate.

Exemplary ionic liquids include but are not limited to phosphonium salts with oligo(ethylene glycol) groups such as:

triethyl((2-methoxyethoxy)methyl)phosphonium bis(trifluoromethylsulfonyl)imide,
triethyl((2-(2-methoxyethoxy)ethoxy)methyl)phosphonium bis(trifluoromethylsulfonyl)imide,
triethyl((2-(2-(2-methoxyethoxy)ethoxy)ethoxy)methyl) phosphonium bis(trifluoromethylsulfonyl)imide,
triethyl((2-methoxyethoxy)methyl)phosphonium bis(fluoromethylsulfonyl)imide,
triethyl((2-(2-methoxyethoxy)ethoxy)methyl)phosphonium bis(fluoromethylsulfonyl)imide,
triethyl((2-(2-(2-methoxyethoxy)ethoxy)ethoxy)methyl) phosphonium bis(fluoromethylsulfonyl)imide,
triethyl((2-methoxyethoxy)methyl)phosphonium bis(oxalato)borate,
triethyl((2-(2-methoxyethoxy)ethoxy)methyl)phosphonium bis(oxalato)borate,
triethyl((2-(2-(2-methoxyethoxy)ethoxy)ethoxy)methyl) phosphonium bis(oxalato)borate,
triethyl((2-methoxyethoxy)methyl)phosphonium hexafluorophosphate,
triethyl((2-(2-methoxyethoxy)ethoxy)methyl)phosphonium hexafluorophosphate, and
triethyl((2-(2-(2-methoxyethoxy)ethoxy)ethoxy)methyl) phosphonium hexafluorophosphate.

Exemplary ionic liquids include but are not limited to phosphonium salts with siloxane groups such as:
triethyl-(methylenepentamethyldisiloxane)phosphonium bis(trifluoromethylsulfonyl)imide,
triethyl-(methyleneheptamethyltrisiloxane)phosphonium bis(trifluoromethylsulfonyl)imide,
triethyl-(methyleneoctamethyltetrasiloxane)phosphonium bis(trifluoromethylsulfonyl)imide,
triethyl-(methylenepentamethyldisiloxane)phosphonium bis(fluoromethylsulfonyl)imide,
triethyl-(methyleneheptamethyltrisiloxane)phosphonium bis(fluoromethylsulfonyl)imide,
triethyl-(methyleneoctamethyltetrasiloxane)phosphonium bis(fluoromethylsulfonyl)imide,
triethyl-(methylenepentamethyldisiloxane)phosphonium bis(oxalato)borate,
triethyl-(methyleneheptamethyltrisiloxane)phosphonium bis(oxalato)borate,
triethyl-(methyleneoctamethyltetrasiloxane)phosphonium bis(oxalato)borate,
triethyl-(methylenepentamethyldisiloxane)phosphonium hexafluorophosphate,
triethyl-(methyleneheptamethyltrisiloxane)phosphonium hexafluorophosphate, and
triethyl-(methyleneoctamethyltetrasiloxane)phosphonium hexafluorophosphate.

Exemplary ionic liquids include but are not limited to phosphonium salts with sulfone groups such as:
triethyl-(2-(methylsulfonyl)ethyl)phosphonium bis(trifluoromethylsulfonyl)imide,
triethyl-(2-(ethylsulfonyl)ethyl)phosphonium bis(trifluoromethylsulfonyl)imide,
triethyl-(2-(propylsulfonyl)ethyl)phosphonium bis(trifluoromethylsulfonyl)imide,
triethyl-(2-(butylsulfonyl)ethyl)phosphonium bis(trifluoromethylsulfonyl)imide,
triethyl-(2-(methylsulfonyl)ethyl)phosphonium bis(fluoromethylsulfonyl)imide,
triethyl-(2-(ethylsulfonyl)ethyl)phosphonium bis(fluoromethylsulfonyl)imide,
triethyl-(2-(propylsulfonyl)ethyl)phosphonium bis(fluoromethylsulfonyl)imide,
triethyl-(2-(butylsulfonyl)ethyl)phosphonium bis(fluoromethylsulfonyl)imide,
triethyl-(2-(methylsulfonyl)ethyl)phosphonium bis(oxalato)borate,
triethyl-(2-(ethylsulfonyl)ethyl)phosphonium bis(oxalato)borate,
triethyl-(2-(propylsulfonyl)ethyl)phosphonium bis(oxalato)borate,
triethyl-(2-(butylsulfonyl)ethyl)phosphonium bis(oxalato)borate,
triethyl-(2-(methylsulfonyl)ethyl)phosphonium hexafluorophosphate,
triethyl-(2-(ethylsulfonyl)ethyl)phosphonium hexafluorophosphate,
triethyl-(2-(propylsulfonyl)ethyl)phosphonium hexafluorophosphate, and
triethyl-(2-(butylsulfonyl)ethyl)phosphonium hexafluorophosphate.

Exemplary ionic liquids include but are not limited to phosphonium salts with carbonate groups such as:
triethyl-3-((2-oxo-1,3-dioxolan-4-yl)methyl)phosphonium bis(trifluoromethylsulfonyl)imide,
triethyl-3-((2-oxo-1,3-dioxolan-4-yl)ethyl)phosphonium bis(trifluoromethylsulfonyl)imide,
triethyl-3-((2-oxo-1,3-dioxolan-4-yl)propyl)phosphonium bis(trifluoromethylsulfonyl)imide,
triethyl-3-((2-oxo-1,3-dioxolan-4-yl)methyl)phosphonium bis(fluoromethylsulfonyl)imide,
triethyl-3-((2-oxo-1,3-dioxolan-4-yl)ethyl)phosphonium bis(fluoromethylsulfonyl)imide,
triethyl-3-((2-oxo-1,3-dioxolan-4-yl)propyl)phosphonium bis(fluoromethylsulfonyl)imide,
triethyl-3-((2-oxo-1,3-dioxolan-4-yl)methyl)phosphonium bis(oxalato)borate,
triethyl-3-((2-oxo-1,3-dioxolan-4-yl)ethyl)phosphonium bis(oxalato)borate,
triethyl-3-((2-oxo-1,3-dioxolan-4-yl)propyl)phosphonium bis(oxalato)borate,
triethyl-3-((2-oxo-1,3-dioxolan-4-yl)methyl)phosphonium hexafluorophosphate,
triethyl-3-((2-oxo-1,3-dioxolan-4-yl)ethyl)phosphonium hexafluorophosphate, and
triethyl-3-((2-oxo-1,3-dioxolan-4-yl)propyl)phosphonium hexafluorophosphate.

In accordance with another aspect, there is provided an electrolyte for use in an energy storage device, the electrolyte comprising a room temperature ionic liquid as described herein.

In some embodiments, the electrolyte includes a lithium salt in addition to the ionic liquid. A variety of lithium salts may be used including for example, $Li[CF_3CO_2]$; $Li[C_2F_5CO_2]$; $Li[ClO_4]$; $Li[BF_4]$; $Li[AsF_6]$; $Li[PF_6]$; $Li[PF_2(C_2O_4)_2]$; $Li[PF_4C_2O_4]$; $Li[CF_3SO_3]$; $Li[N(CF_3SO_2)_2]$; $Li[C(CF_3SO_2)_3]$; $Li[N(SO_2C_2F_5)_2]$; lithium alkyl fluorophosphates; $Li[B(C_2O_4)_2]$; $Li[BF_2C_2O_4]$; $Li_2[B_{12}Z_{12-j}H_j]$; $Li_2[B_{10}X_{10-j'}H_{j'}]$; or a mixture of any two or more thereof, wherein Z is independently at each occurrence a halogen, j is an integer from 0 to 12 and j' is an integer from 1 to 10.

In some embodiments, the concentration of the lithium salt present in the ionic liquid ranges from about 0.01 M to about 1.5 M, from about 0.05 M to about 1.2 M, or from about 0.4 M to about 1.0 M. If the concentration of the ionic electrolyte salt is less than about 0.01 M, the ionic conductivity of the resulting non-aqueous electrolyte tends to decrease due to an inadequate number of carrier ions in the electrolyte.

In some applications of the present electrolyte, such as a formulation for a lithium ion battery, aprotic solvents are combined with the present ionic liquids to decrease the viscosity and increase the conductivity. Aprotic solvents lack exchangeable protons and include cyclic carbonic acid esters, linear carbonic acid esters, phosphoric acid esters, oligoether substituted siloxanes/silanes, cyclic ethers, chain ethers, lactone compounds, chain esters, nitrile compounds, amide compounds, sulfone compounds and the like. These solvents may be used singly, or at least two of them in admixture. Examples of aprotic solvents or carriers for forming the electrolyte systems include but are not limited to dimethyl carbonate, ethyl methyl carbonate, diethyl carbonate, methyl propyl carbonate, ethyl propyl carbonate, dipropyl carbonate, bis(trifluoroethyl) carbonate, bis(pentafluoropropyl) carbonate, trifluoroethyl methyl carbonate, pentafluoroethyl methyl carbonate, heptafluoropropyl methyl carbonate, perfluorobutyl methyl carbonate, trifluoroethyl ethyl carbonate, pentafluoroethyl ethyl carbonate, heptafluoropropyl ethyl carbonate, perfluorobutyl ethyl carbonate, etc., fluorinated oligomers, dimethoxyethane, triglyme, dimethylvinylene carbonate, tetraethyleneglycol, dimethyl ether, polyethylene glycols, sulfones, and gamma-butyrolactone.

In some embodiments, the inventive electrolytes further include an electrode stabilizing additive to protect the electrodes from degradation. Thus, electrolytes of the present technology can include an electrode stabilizing additive that can be reduced or polymerized on the surface of a negative electrode to form a passivation film on the surface of the negative electrode. Likewise, inventive electrolytes can include an electrode stabilizing additive that can be oxidized or polymerized on the surface of the positive electrode to form a passivation film on the surface of the positive electrode. In some embodiments, electrolytes of the present technology further include mixtures of the two types of electrode stabilizing additives. The additives are typically present at a concentration of about 0.001 to 8 wt %.

In some embodiments, an electrode stabilizing additive is a substituted or unsubstituted linear, branched or cyclic hydrocarbon comprising at least one oxygen atom and at least one aryl, alkenyl or alkynyl group. The passivating film formed from such electrode stabilizing additives may also be formed from a substituted aryl compound or a substituted or unsubstituted heteroaryl compound where the additive comprises at least one oxygen atom. Alternatively, a combination of two additives may be used. In some such embodiments, one additive is selective for forming a passivating film on the cathode to prevent leaching of metal ions and the other additive can be selective for passivating the anode surface to prevent or lessen the reduction of metal ions at the anode.

Representative electrode stabilizing additives include 1,2-divinyl furoate, 1,3-butadiene carbonate, 1-vinylazetidin-2-one, 1-vinylaziridin-2-one, 1-vinylpiperidin-2-one, 1 vinylpyrrolidin-2-one, 2,4-divinyl-1,3-dioxane, 2 amino-3 vinylcyclohexanone, 2-amino-3-vinylcyclopropanone, 2 amino-4-vinylcyclobutanone, 2-amino-5-vinylcyclopentanone, 2-aryloxy-cyclopropanone, 2-vinyl-[1,2]oxazetidine, 2 vinylaminocyclohexanol, 2-vinylaminocyclopropanone, 2 vinyloxetane, 2-vinyloxy-cyclopropanone, 3-(N-vinylamino)cyclohexanone, 3,5-divinyl furoate, 3-vinylazetidin-2-one, 3 vinylaziridin 2 one, 3 vinylcyclobutanone, 3 vinylcyclopentanone, 3 vinyloxaziridine, 3 vinyloxetane, 3-vinylpyrrolidin-2-one, 4,4 divinyl-3 dioxolan 2-one, 4 vinyltetrahydropyran, 5-vinylpiperidin-3-one, allylglycidyl ether, butadiene monoxide, butyl vinyl ether, dihydropyran-3-one, divinyl butyl carbonate, divinyl carbonate, divinyl crotonate, divinyl ether, divinyl ethylene carbonate, divinyl ethylene silicate, divinyl ethylene sulfate, divinyl ethylene sulfite, divinyl methoxypyrazine, divinyl methylphosphate, divinyl propylene carbonate, ethyl phosphate, methoxy-o-terphenyl, methyl phosphate, oxetan-2-yl-vinylamine, oxiranylvinylamine, vinyl carbonate, vinyl crotonate, vinyl cyclopentanone, vinyl ethyl-2-furoate, vinyl ethylene carbonate, vinyl ethylene silicate, vinyl ethylene sulfate, vinyl ethylene sulfite, vinyl methacrylate, vinyl phosphate, vinyl-2-furoate, vinylcylopropanone, vinylethylene oxide, β-vinyl-γ-butyrolactone, or a mixture of any two or more thereof. In some embodiments the electrode stabilizing additive may be a cyclotriphosphazene that is substituted with F, alkyloxy, alkenyloxy, aryloxy, methoxy, allyloxy groups, or combinations thereof. For example, the additive may be a (divinyl)-(methoxy)(trifluoro)cyclotriphosphazene, (trivinyl)(difluoro)(methoxy)cyclotriphosphazene, (vinyl)(methoxy)(tetrafluoro)cyclotriphosphazene, (aryloxy)(tetrafluoro)(methoxy)cyclotriphosphazene, (diaryloxy)(trifluoro)(methoxy)cyclotriphosphazene compounds, or a mixture of two or more such compounds. In some embodiments, the electrode stabilizing additive is vinyl ethylene carbonate, vinyl carbonate, or 1,2-diphenyl ether, or a mixture of any two or more such compounds.

Other representative electrode stabilizing additives may include compounds with phenyl, naphthyl, anthracenyl, pyrrolyl, oxazolyl, furanyl, indolyl, carbazolyl, imidazolyl, or thiophenyl groups. For example, electrode stabilizing additives may be aryloxpyrrole, aryloxy ethylene sulfate, aryloxy pyrazine, aryloxy-carbazole trivinylphosphate, aryloxy-ethyl-2-furoate, aryloxy-o-terphenyl, aryloxy-pyridazine, butyl-aryloxy-ether, divinyl diphenyl ether, (tetrahydrofuran-2-yl)-vinylamine, divinyl methoxybipyridine, methoxy-4-vinylbiphenyl, vinyl methoxy carbazole, vinyl methoxy piperidine, vinyl methoxypyrazine, vinyl methyl carbonate-allylanisole, vinyl pyridazine, 1-divinylimidazole, 3-vinyltetrahydrofuran, divinyl furan, divinyl methoxy furan, divinylpyrazine, vinyl methoxy imidazole, vinylmethoxy pyrrole, vinyl-tetrahydrofuran, 2,4-divinyl isooxazole, 3,4 divinyl-1-methyl pyrrole, aryloxyoxetane, aryloxy-phenyl carbonate, aryloxy-piperidine, aryloxy-tetrahydrofuran, 2-aryl-cyclopropanone, 2-diaryloxy-furoate, 4-allylanisole, aryloxy-carbazole, aryloxy-2-furoate, aryloxy-crotonate, aryloxy-cyclobutane, aryloxy-cyclopentanone, aryloxy-cyclopropanone, aryloxy-cycolophosphazene, aryloxy-ethylene silicate, aryloxy-ethylene sulfate, aryloxy-ethylene sulfite, aryloxy-imidazole, aryloxy-methacrylate, aryloxy-phosphate, aryloxy-pyrrole, aryloxyquinoline, diaryloxycyclotriphosphazene, diaryloxy ethylene carbonate, diaryloxy furan, diaryloxy methyl phosphate, diaryloxy-butyl carbonate, diaryloxy-crotonate, diaryloxy-diphenyl ether, diaryloxy-ethyl silicate, diaryloxy-ethylene silicate, diaryloxy-ethylene sulfate, diaryloxyethylene sulfite, diaryloxy-phenyl carbonate, diaryloxy-propylene carbonate, diphenyl carbonate, diphenyl diaryloxy silicate, diphenyl divinyl silicate, diphenyl ether, diphenyl silicate, divinyl methoxydiphenyl ether, divinyl phenyl carbonate, methoxycarbazole, or 2,4-dimethyl-6-hydroxy-pyrimidine, vinyl methoxyquinoline, pyridazine, vinyl pyridazine, quinoline, vinyl quinoline, pyridine, vinyl pyridine, indole, vinyl indole, triethanolamine, 1,3-dimethyl butadiene, butadiene, vinyl ethylene carbonate, vinyl carbonate, imidazole, vinyl imidazole, piperidine, vinyl piperidine, pyrimidine, vinyl pyrimidine, pyrazine, vinyl pyrazine, isoquinoline, vinyl isoquinoline, quinoxaline, vinyl quinoxaline, biphenyl, 1,2-diphenyl ether, 1,2-diphenylethane, o terphenyl, N-methyl pyrrole, naphthalene, or a mixture of any two or more such compounds.

In some other embodiments, the electrolyte of the present technology includes an aprotic gel polymer carrier/solvent. Suitable gel polymer carrier/solvents include polyethers, polyethylene oxides, polyimides, polyphosphazines, polyacrylonitriles, polysiloxanes, polyether grafted polysiloxanes, derivatives of the foregoing, copolymers of the foregoing, cross-linked and network structures of the foregoing, blends of the foregoing, and the like, to which is added a suitable ionic electrolyte salt. Other gel-polymer carrier/solvents include those prepared from polymer matrices derived from polypropylene oxides, polysiloxanes, sulfonated polyimides, perfluorinated membranes (Nafion resins), divinyl polyethylene glycols, polyethylene glycol-bis-(methyl acrylates), polyethylene glycol-bis(methyl methacrylates), derivatives of the foregoing, copolymers of the foregoing, cross-linked and network structures of the foregoing.

The inventive functional ionic liquids and the electrolytic solution containing the salt are high in electrical conductivity and solubility in organic solvents, and are suitable for use as an electrolytic solution for electrochemical devices. Examples of electrochemical devices are electric double-layer capacitor, secondary batteries, solar cells of the pigment sensitizer type, electrochromic devices, condenser, etc., which are nevertheless not limitative. Especially suitable as electrochemical devices are electric double-layer capacitor and secondary batteries such as lithium ion battery.

In yet another aspect, an electrochemical device is provided that includes a cathode; an anode; and an electrolyte including an ionic liquid as described herein. In one embodiment, the electrochemical device is a lithium secondary battery. In some embodiments, the secondary battery is a lithium battery, a lithium-ion battery, a lithium-sulfur battery, a lithium-air battery, a sodium ion battery, or a magnesium battery. In some embodiments, the electrochemical device is an electrochemical cell such as a capacitor. In some embodiments, the capacitor is an asymmetric capacitor or supercapacitor. In some embodiments, the electrochemical cell is a primary cell. In some embodiments, the primary cell that is a lithium/$MnO_2$ battery or Li/poly(carbon monofluoride) battery. In some embodiments, the electrochemical cell is a solar cell.

Suitable cathodes include those such as, but not limited to, a lithium metal oxide, spinel, olivine, carbon-coated olivine, $LiFePO_4$, $LiCoO_2$, $LiNiO_2$, $LiNi_{1-x}Co_yMet_zO_2$, $LiMn_{0.5}Ni_{0.5}O_2$, $LiMn_{0.3}Co_{0.3}Ni_{0.3}O_2$, $LiMn_2O_4$, $LiFeO_2$, $Li_{1+x}Ni_\alpha Mn_\beta Co_\gamma Met'_\delta O_{2-z}F_z$, $A_nB_2(XO_4)_3$ (NASICON), vanadium oxide; lithium peroxide, sulfur, polysulfide, a lithium carbon monofluoride (also known as LiCFx), or mixtures of any two or more thereof, where Met is Al, Mg, Ti, B, Ga, Si, Mn, or Co; Met' is Mg, Zn, Al, Ga, B, Zr, or Ti; A is Li, Ag, Cu, Na, Mn, Fe, Co, Ni, Cu, or Zn; B is Ti, V, Cr, Fe, or Zr; X is P, S, Si, W, or Mo; $0 \leq x \leq 0.3$, $0 \leq y \leq 0.5$, $0 \leq z \leq 0.5$, $0 \leq x' \leq 0.4$, $0 \leq \alpha \leq 1$, $0 \leq \beta \leq 1$, $0 \leq \gamma \leq 1$, $0 \leq \delta \leq 0.4$, and $0 \leq z' \leq 0.4$; and $0 \leq h' \leq 3$. According to some embodiments, the spinel is a spinel manganese oxide with the formula of $Li_{1+x}Mn_{2-z}Met'''_yO_{4-m}X'_n$, wherein Met''' is Al, Mg, Ti, B, Ga, Si, Ni, or Co; X' is S or F; and wherein $0 \leq x \leq 0.3$, $0 \leq y \leq 0.5$, $0 \leq z \leq 0.5$, $0 \leq m \leq 0.5$ and $0 \leq n \leq 0.5$. In other embodiments, the olivine has a formula of $Li_{1+x}Fe_{1-z}Met''_yPO_{4-m}X'_n$, wherein Met'' is Al, Mg, Ti, B, Ga, Si, Ni, Mn or Co; X' is S or F; and wherein $0 \leq x \leq 0.3$, $0 \leq y \leq 0.5$, $0 \leq z \leq 0.5$, $0 \leq m \leq 0.5$ and $0 \leq n \leq 0.5$.

Suitable anodes include those such as lithium metal; graphitic materials, amorphous carbon, $Li_4Ti_5O_{12}$, tin alloys, silicon alloys, intermetallic compounds, or mixtures of any two or more such materials. Suitable graphitic materials including natural graphite, artificial graphite, graphitized meso-carbon microbeads (MCMB), and graphite fibers, as well as any amorphous carbon materials. In some embodiments, the anode and cathode are separated from each other by a porous separator.

The separator for the lithium battery often is a microporous polymer film. Examples of polymers for forming films include: nylon, cellulose, nitrocellulose, polysulfone, polyacrylonitrile, polyvinylidene fluoride, polypropylene, polyethylene, polybutene, or co-polymers or blends of any two or more such polymers. In some instances, the separator is an electron beam treated micro-porous polyolefin separator. The electron treatment can improve the deformation temperature of the separator and can accordingly enhance the high temperature performance of the separator. Additionally, or alternatively, the separator can be a shut-down separator. The shut-down separator can have a trigger temperature above 130° C. to permit the electrochemical cells to operate at temperatures up to 130° C.

One skilled in the art will readily realize that all ranges discussed can and do necessarily also describe all subranges therein for all purposes and that all such subranges also form part and parcel of this present technology. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc.

All publications, patent applications, issued patents, and other documents referred to in this specification are herein incorporated by reference as if each individual publication, patent application, issued patent, or other document was specifically and individually indicated to be incorporated by reference in its entirety. Definitions that are contained in text incorporated by reference are excluded to the extent that they contradict definitions in this disclosure.

The present technology, thus generally described, will be understood more readily by reference to the following examples, which are provided by way of illustration and are not intended to be limiting of the present technology.

EXAMPLES

Ionic liquids of the present technology may be synthesized by various methods known in the art. For example, to prepare cationic phosphonium, imidazolium, pyridinium, or quaternary ammonium-based ionic liquids, the corresponding phosphite, 1-subsituted imidazole, pyridine, or tertiary amine may be reacted with a suitable electrophile under alkylating conditions and then reacted with a suitable lithium salt (i.e., LiX where X is defined as herein). Suitable electrophiles include R groups (as defined herein) bearing, e.g., a halide, mesylate, triflate or similar leaving group. By way of non-limiting example, Scheme 1 shows the synthesis of representative ionic liquids of the present technology. Preparation of oxazolium and thizolium-based ionic liquids is similar, but requires deprotonation of the corresponding oxazole or thiazole with an appropriate base, e.g., an alkali metal hydride prior to reaction with the electrophile.

Scheme 1. Representative synthesis of functionalized ionic liquids IL1-I, IL1-TFSI, IL2-I, IL2-TFSI, IL3-Br and IL3-TFSI.

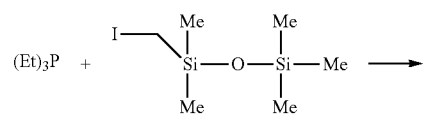

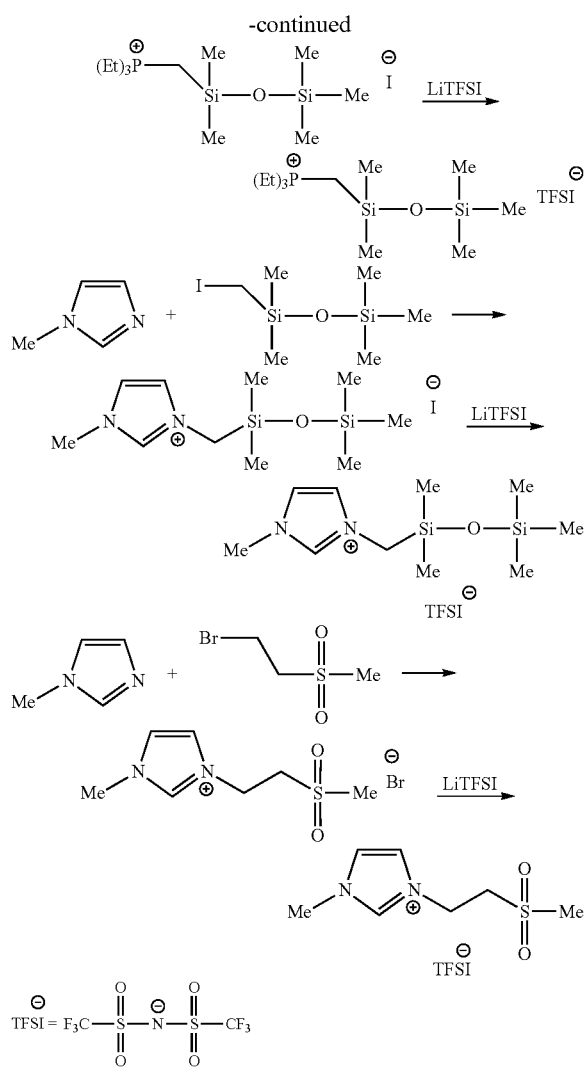

Example 1

Synthesis of IL1-I

Figure 1B:
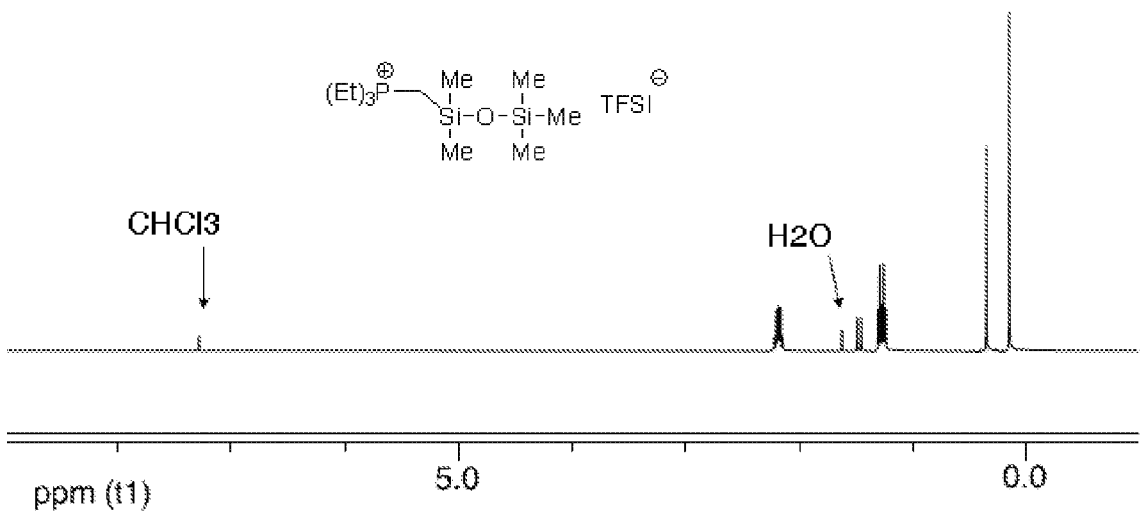

A mixture consisting of equimolar quantities of triethylphosphine (20 g, 0.17 mmol) and ICH$_2$SiMe$_2$OSiMe$_3$ (48 g, 0.17 mmol) was stirred at room temperature for 24 h. The resulting solid was washed three times with hexane then diethyl ether and placed under vacuum to afford IL1-I. Yield: 49 g (72%). $^1$H NMR (CDCl$_3$) is shown in FIG. 1.

Example 2

Synthesis of IL1-TFSI

A solution of IL1-I (48.8 g, 0.16 mol) in water (300 mL) was treated with lithium bis(trifluoromethanesulfonyl)imide (LiTFSI) (44.6 g, 0.17 mol). The solution was allowed to stir at room temperature for a period of 12 h at which time the room temperature ionic liquid IL1-TFSI formed a second layer at the bottom of the flask. IL1-TFSI was dissolved in CH$_2$Cl$_2$, and washed with deionized water until no residual I$^-$ in the rinse can be detected by 0.1 M AgNO$_3$ solution. The CH$_2$Cl$_2$ was stirred with carbon black and Al$_2$O$_3$ for 2 h and filtered. The crude product was dried under high vacuum (0.02 torr) at 100° C. for 16 h. Yield: 50 g (75%). $^1$H NMR (CDCl$_3$) is shown in FIG. 1

Example 3

Synthesis of IL2-I

Figure 2A:
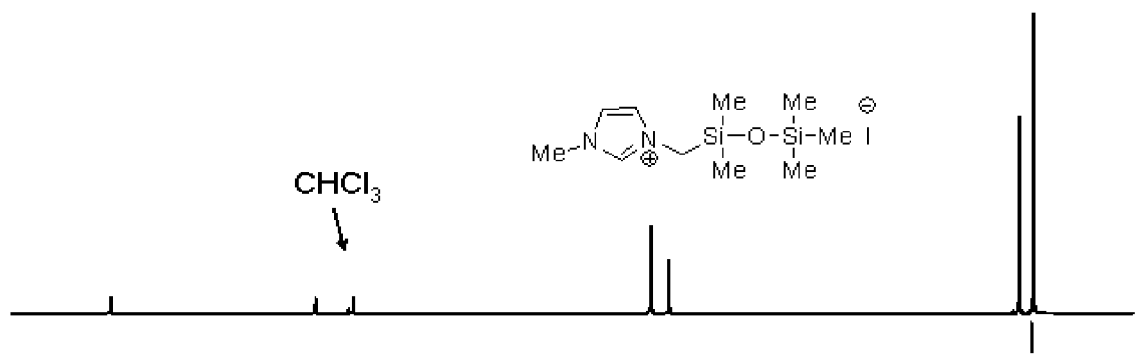
FIGS. 2A and 2B. $^1$H-NMR of 1-ethyl-3-(methylenepentamethyldisiloxane) imidazolium iodide (IL2-I, FIG. 2A) and 1-ethyl-3-(methylenepentamethyldisiloxane)-1H-imidazol-3-ium bis(trifluoromethanesulfonyl)imide (IL2-TFSI, 2B).
Figure 2B:
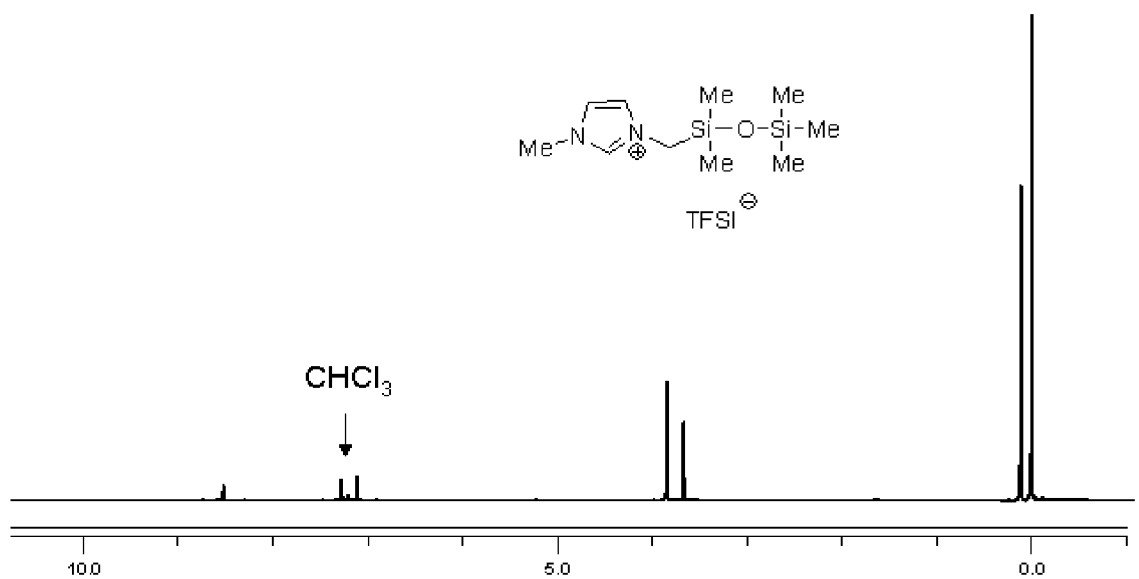

Freshly distilled ICH$_2$SiMe$_2$OSiMe$_3$ (48.7 g, 0.16 mol) was added in one portion to a 500 mL thick walled glass reactor containing 1-methyl imidazole (13.9 g, 0.16 mol) equipped with a magnetic stirrer and a water cooled condenser. The solution was stirred for 16 h at 100° C. The solution was cooled down to room temperature and stirred with hexane. The precipitate was filtered and washed several times with hexane and diethyl ether, dried overnight under vacuum. Yield for IL2-I: 60.5 g (95%). $^1$H NMR (CDCl$_3$) is shown in FIG. 2.

Example 4

Synthesis of IL2-TFSI

A solution of lithium bis(trifluoromethanesulfonyl)imide (46.4 g, 0.16 mol) in 100 mL of H$_2$O was added dropwise to a solution of IL2-I (59.8 g, 0.16 mol) in 150 mL of H$_2$O. The solution was stirred at ambient temperature for 12 h. Dichloromethane (250 mL) was added, and the mixture was transferred to a separatory funnel. The lower phase (ionic liquid+CH$_2$Cl$_2$) was collected. The ionic liquid was purified through a short alumina column, and the CH$_2$Cl$_2$ removed on a rotary evaporator. The resultant hydrophobic liquid was washed three times with 150 mL of H$_2$O and dried for 12 h at 100° C. under vacuum to afford IL2-TFSI (69 g, 80% yield) as a pale yellow liquid. $^1$H NMR (CDCl$_3$) is shown in FIG. 2

Example 5

Synthesis of IL3-Br

Figure 3A:
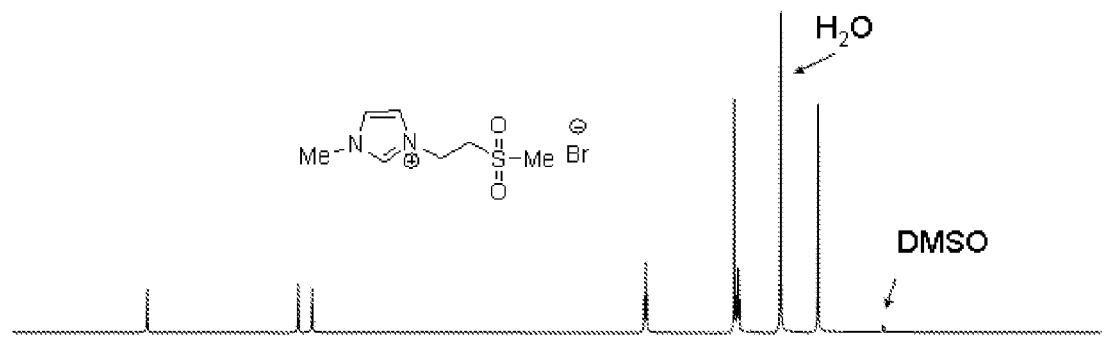
FIGS. 3A and 3B. $^1$H-NMR of 1-ethyl-3-(ethylenemethylsulfone)-1H-imidazol-3-ium bromide (IL3-Br, FIG. 3A) and 1-ethyl-3-(ethylenemethylsulfone)-1H-imidazol-3-ium bis(trifluoro-methanesulfonyl)imide (IL3-TFSI, FIG. 3B).
Figure 3B:
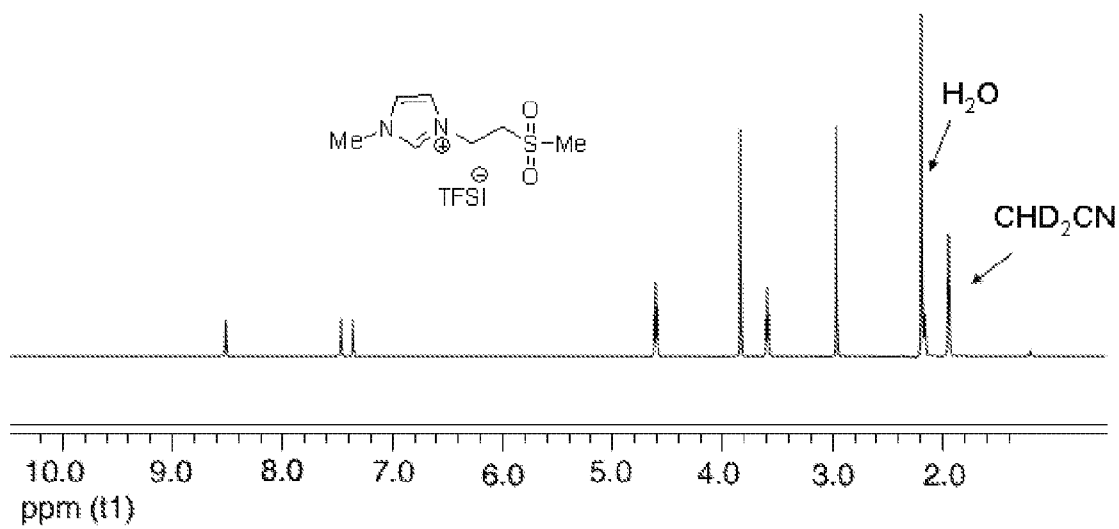

BrCH$_2$CH$_2$SO$_2$Me (14.3 g, 0.076 mol) was added in one portion to a 250 mL round bottom flask containing 1-methyl imidazole (6.3 g, 0.076 mol) equipped with a magnetic stirrer and a water cooled condenser. The solution was stirred for 16 h at 100° C. The oil residue was treated with CH$_3$CN to precipitate the product. The precipitate was filtered and washed several times with pre-cooled CH$_3$CN, dried overnight under vacuum. Yield for IL2-I: 12.4 g (60%). $^1$H NMR (DMSO d$_6$) is shown in FIG. 3.

Example 6

Synthesis of IL3-TFSI

A solution of lithium bis(trifluoromethanesulfonyl)imide (13.2 g, 0.046 mol) in 60 mL of H$_2$O was added dropwise to a solution of IL2-I (12.4 g, 0.046 mol) in 100 mL of H$_2$O. The solution was stirred at ambient temperature for 12 h. Methylene dichloride (500 mL) was added, and all was transferred to a separatory funnel. The lower phase (ionic liquid+CH$_2$Cl$_2$) was collected. Ionic liquid was purified through a short alumina column, and the CH$_2$Cl$_2$ removed on a rotary evaporator. The resultant hydrophobic liquid was washed three times with 150 mL of H$_2$O and dried for 12 h at 100° C. under vacuum to afford IL3-TFSI (10.2 g, 53% yield) as a colorless liquid. $^1$H NMR (CD$_3$CN) is shown in FIG. 3.

Example 7

Comparative Example, Li/MCMB Half Cell Charge Discharge Profiles

Figure 4:
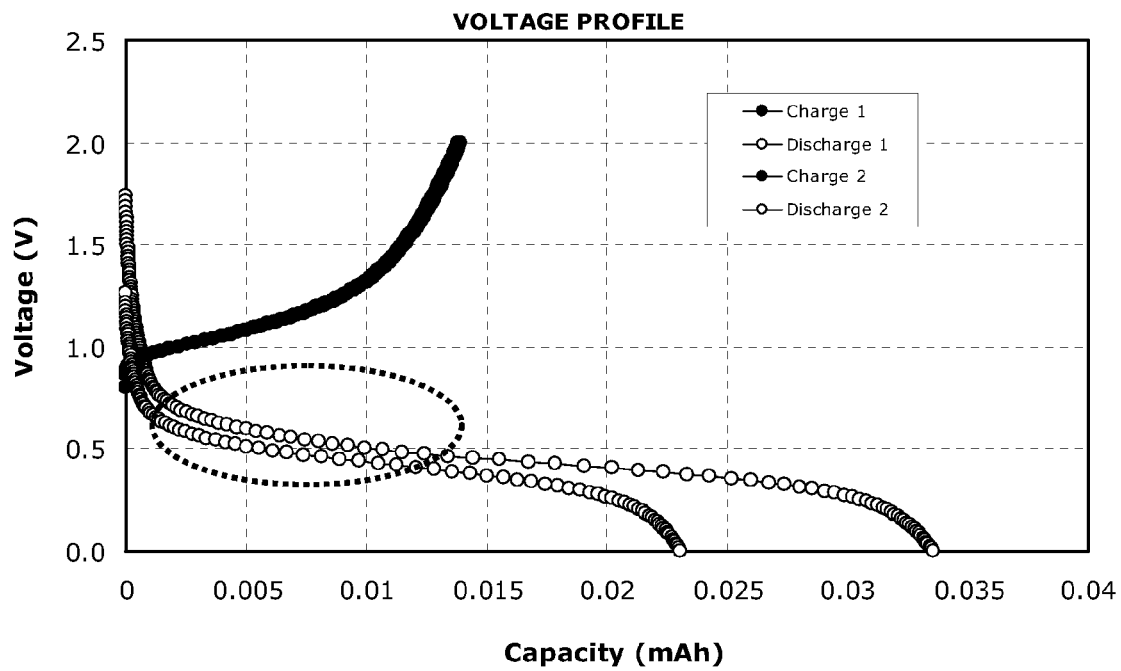
FIG. 4. Li/MCMB half cell charge discharge profiles using conventional 0.8M LiTFSI in tetraethylphosphonium bis(trifluoromethanesulfonyl)imide ionic liquid.

Li/MCMB half cell charge discharge profiles were measured using 0.8M LiTFSI in conventional tetraethylphosphonium bis(trifluoromethanesulfonyl)imide ionic liquid. See FIG. 4. The charging curve showed that no regular intercalation of Li was observed. Instead, it showed a plateau at higher potential at 0.5V vs $Li^+/Li$ indicating ionic liquid co-intercalation/reduction reaction on the MCMB electrode.

Example 8

Figure 5:
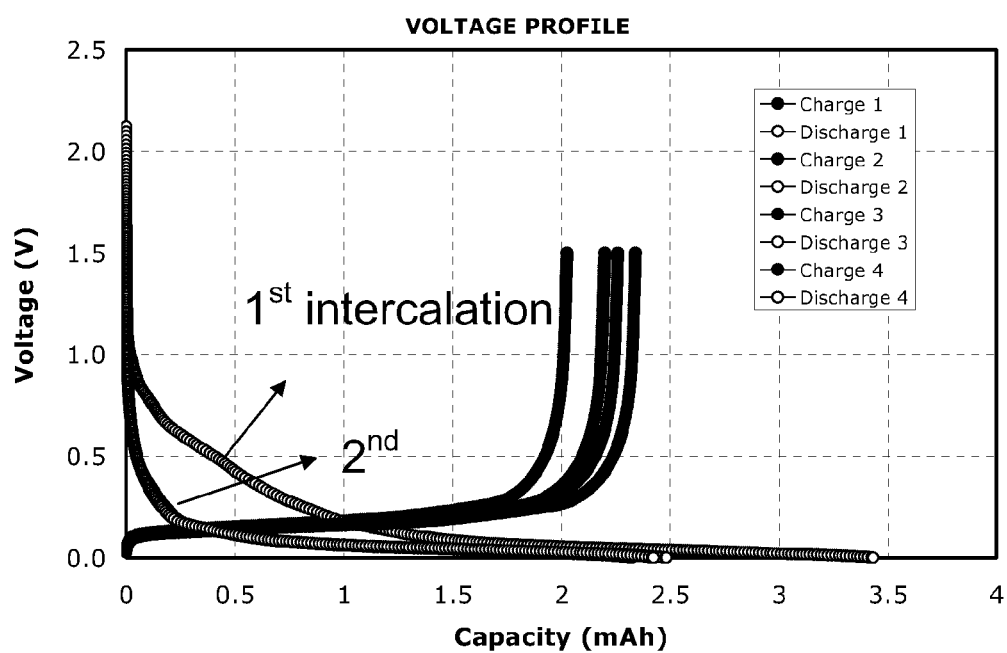
FIG. 5. Li/MCMB half cell charge discharge profiles using 0.8M LiTFSI in triethyl-(methylenepentamethyldisiloxane) phosphonium bis(trifluoromethylsulfonyl)imide (IL1-TFSI).

Li/MCMB Half Cell Charge Discharge Profiles, FIG. 5

Li/MCMB half cell charge discharge profiles using 0.8M LiTFSI in triethyl-(methylenepentamethyldisiloxane)phosphonium bis(trifluoromethylsulfonyl)imide (IL1-TFSI). The $1^{st}$ cycle charging curve showed that a solid electrolyte interphase formation (SEI) starting at 0.8V. The $2^{nd}$ cycle and subsequent cycles are showed regular lithium interaction and de-intercalation on the MCMB electrode. This is a good example that introduction of some functional ionic liquid (Si—O—Si unit in this case) has SEI formation capability and the new IL is completely compatible with graphite based material.

Figure 6:
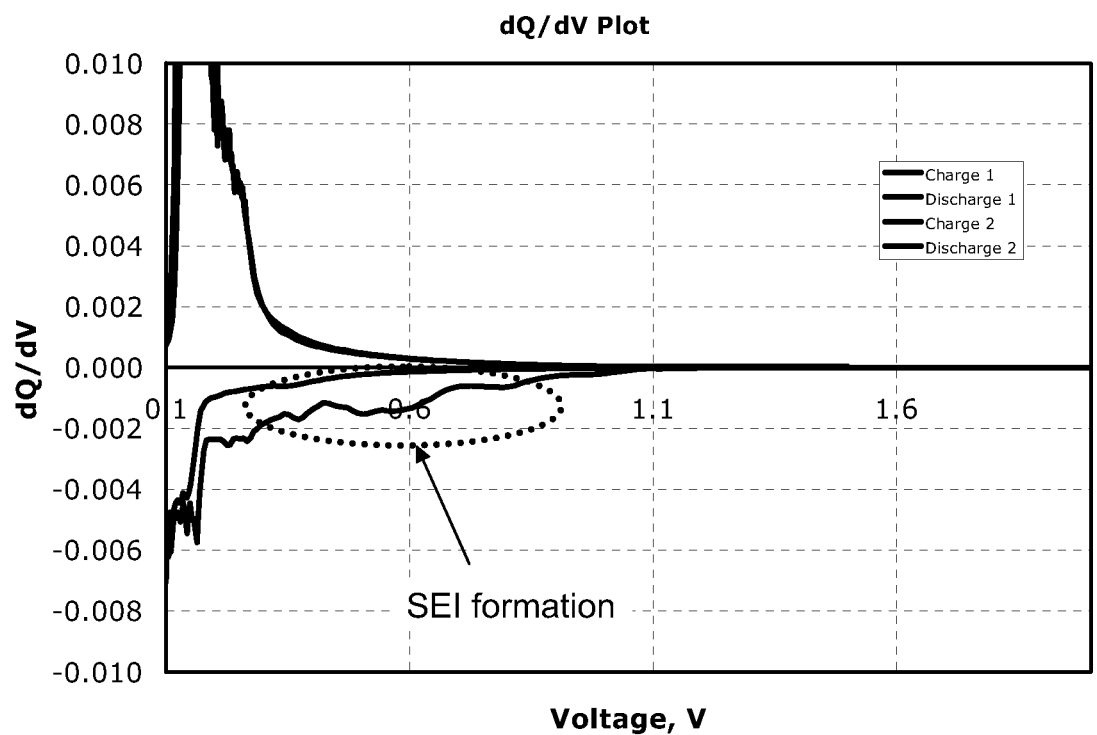
FIG. 6. dQdV profile of Li/MCMB half cell using 0.8M LiTFSI in triethyl-(methylenepentamethyldisiloxane)phosphonium bis(trifluoromethylsulfonyl)imide (IL1-TFSI).

Example 9 dQdV Profile of Li/MCMB Half Cell, FIG. 6 dQdV profile of Li/MCMB half cell using 0.8M LiTFSI in triethyl-(methylenepentamethyldisiloxane)phosphonium bis (trifluoromethylsulfonyl)imide (IL1-TFSI). dQdV curves clearly shows the reduction of the functional ionic liquid passiviating the surface of the graphite electrode. This self SEI formation capability can provide a easy solution to address the issue of IL compatibility with graphite electrode.

Example 10

Figure 7:
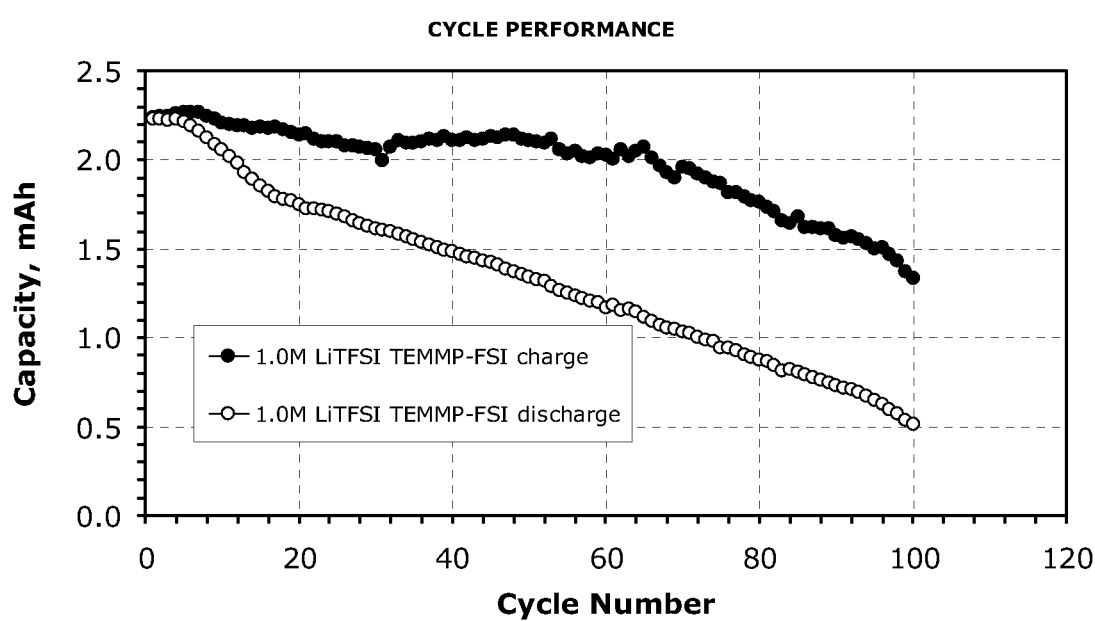
FIG. 7. $LiNi_{0.8}Co_{0.15}Al_{0.05}O_2$/Li half cell charge discharge cycling performance using conventional 0.8M LiTFSI in tetraethylphosphonium bis(trifluoromethanesulfonyl)imide ionic liquid.

Comparative Example, $LiNi_{0.8}Co_{0.15}Al_{0.05}O_2$/Li Half Cell Charge Discharge Profile, FIG. 7

$LiNi_{0.8}Co_{0.15}Al_{0.05}O_2$/Li half cell charge discharge cycling performance using conventional 0.8M LiTFSI in tetraethylphosphonium bis(trifluoromethanesulfonyl)imide ionic liquid. The conventional IL can not provide high efficiency in the cycling test of the positive half cell.

Example 11

Figure 8:
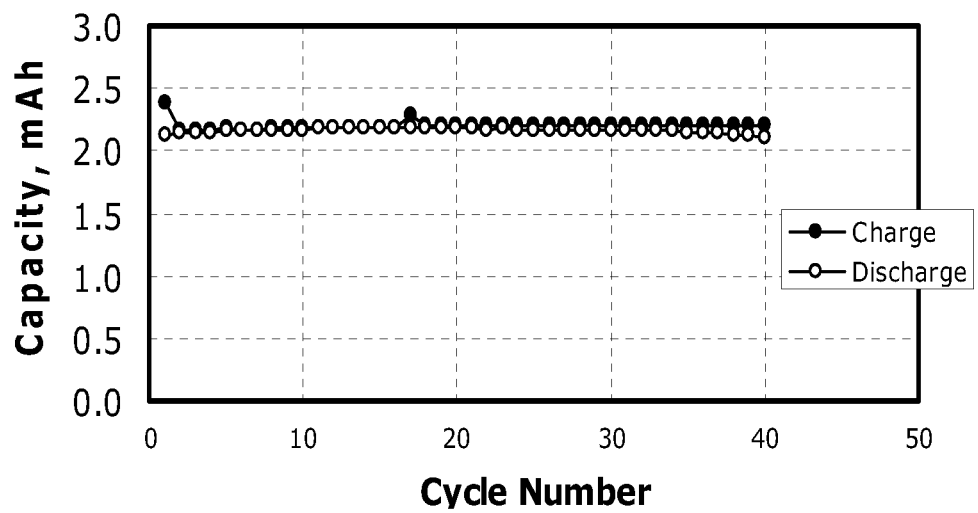
FIG. 8. $LiNi_{0.8}Co_{0.15}Al_{0.05}O_2$/Li half cell charge discharge cycling performance using 0.8M LiTFSI in triethyl-(methylenepentamethyldisiloxane)phosphonium bis(trifluoromethylsulfonyl)imide (IL1-TFSI) at 55° C.
Figure 9:
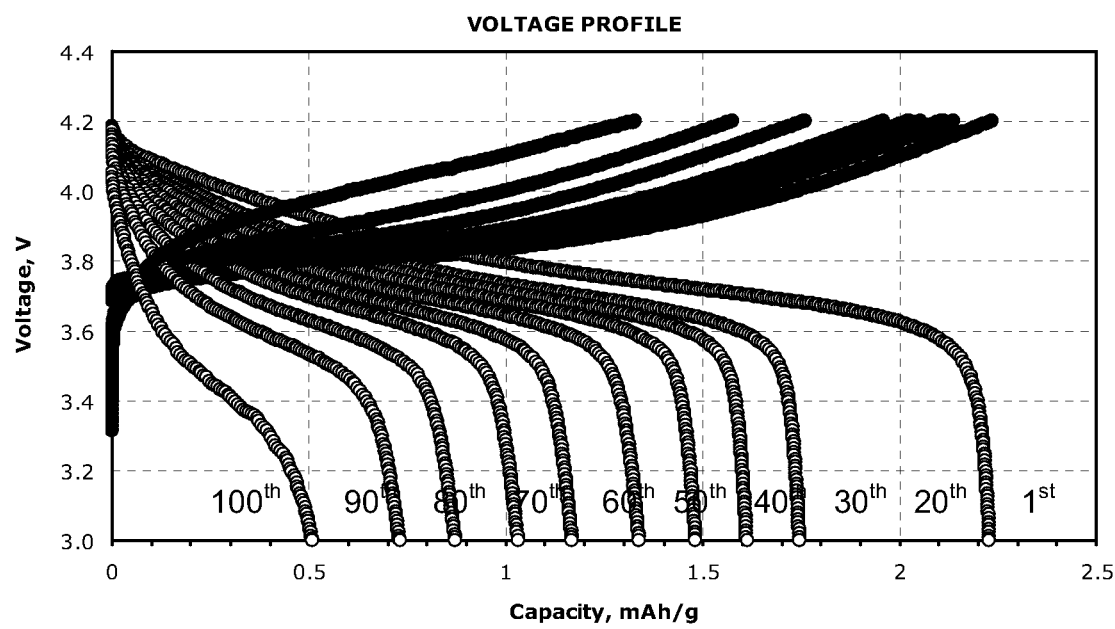
FIG. 9. MCMB/Li half cell charge discharge cycling performance using conventional 0.8M LiTFSI in tetraethylphosphonium bis(trifluoromethanesulfonyl)imide ionic liquid.

$LiNi_{0.8}Co_{0.15}Al_{0.05}O_2$/Li Half Cell Charge Discharge Profile, FIG. 8

$LiNi_{0.8}Co_{0.15}Al_{0.05}O_2$/Li half cell charge discharge cycling performance using 0.8M LiTFSI in triethyl-(methylenepentamethyldisiloxane)phosphonium bis(trifluoromethylsulfonyl)imide (IL1-TFSI) at 55° C. The inventive functional ionic liquid can provide excellent compatibility with lithium oxide cathode material, which is impossible for the conventional IL as indicated in FIG. 7.

Example 12

FIG. 9

MCMB/Li half cell charge discharge cycling performance using conventional 0.8M LiTFSI in tetraethylphosphonium bis(trifluoromethanesulfonyl)imide ionic liquid. Using conventional ionic liquid, the capacity of the MCMB half cell dramatically decreases with cycle number.

Example 13

Figure 10:
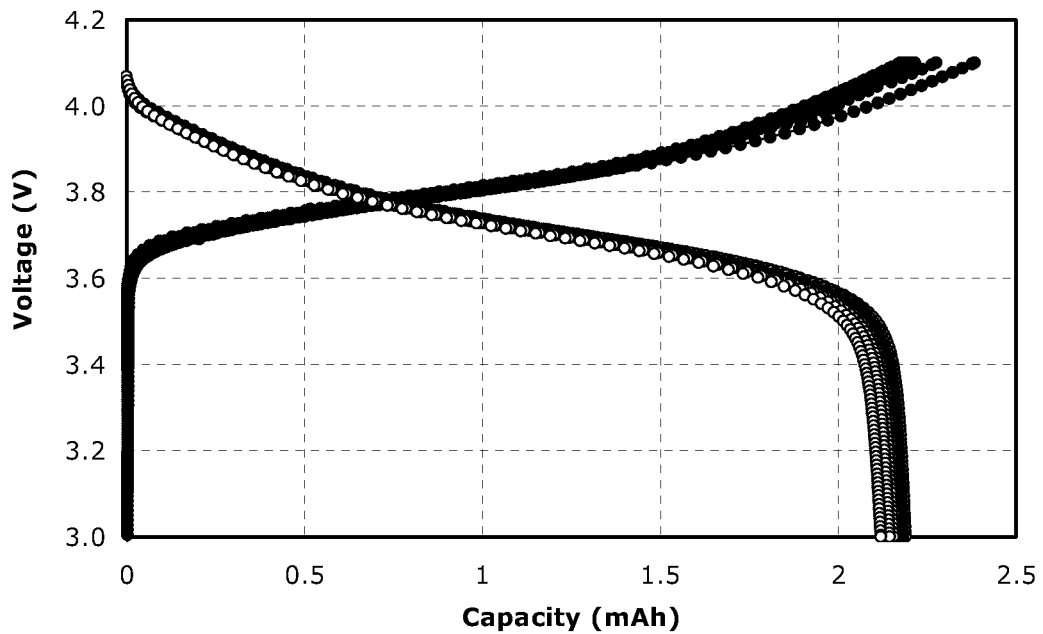
FIG. 10. MCMB/Li half cell charge discharge cycling performance using 0.8M LiTFSI in triethyl-(methylenepentamethyldisiloxane)phosphonium bis(trifluoromethylsulfonyl) imide (IL1-TFSI).

Li/MCMB Half Cell Charge Discharge Profiles, FIG. 10

MCMB/Li half cell charge discharge cycling performance using 0.8M LiTFSI in triethyl-(methylenepentamethyldisiloxane)phosphonium bis(trifluoromethylsulfonyl)-imide (IL1-TFSI). The functionalized ionic liquid showed reversible charge/discharge performance.

Example 14

Figure 11:
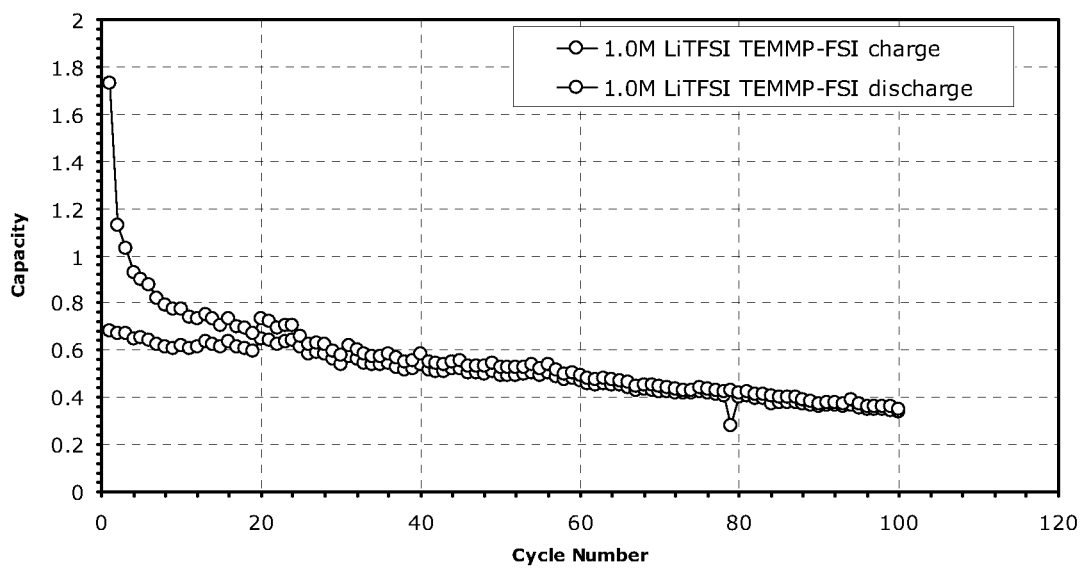
FIG. 11. MCMB/$LiNi_{0.80}Ni_{0.15}Al_{0.05}O_2$ full cell charge discharge cycling performance using conventional 0.8M LiTFSI in tetraethylphosphonium bis(trifluoromethanesulfonyl)imide ionic liquid.

$MCMB/LiNi_{0.80}Ni_{0.15}Al_{0.05}O_2$ Full Cell Charge Discharge Profiles, FIG. 11

$MCMB/LiNi_{0.80}Ni_{0.15}Al_{0.05}O_2$ full cell charge discharge cycling performance using conventional 0.8M LiTFSI in tetraethylphosphonium bis(trifluoromethanesulfonyl)imide ionic liquid. Poor capacity retention was observed for the conventional ionic liquid in a full lithium ion cell.

Example 15

Figure 12:
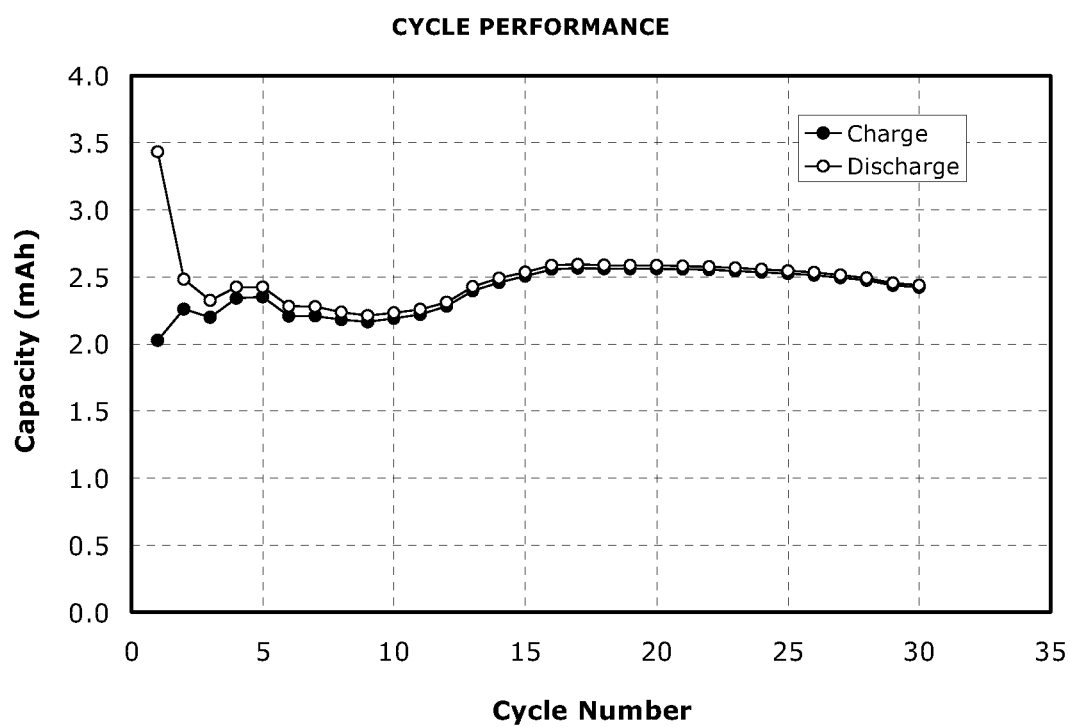
FIG. 12. MCMB/$LiNi_{0.85}Co_{0.15}Al_{0.05}O_2$ full cell charge discharge cycling performance using 0.8M LiTFSI in triethyl-(methylenepentamethyldisiloxane)phosphonium bis (trifluoromethylsulfonyl)imide (IL1-TFSI).

$MCMB/LiNi_{0.85}Ni_{0.15}Al_{0.05}O_2$, Full Cell Charge Discharge Profiles, FIG. 12

$MCMB/LiNi_{0.85}Co_{0.15}Al_{0.05}O_2$ full cell charge discharge cycling performance using 0.8M LiTFSI in triethyl-(methylenepentamethyldisiloxane)phosphonium bis(trifluoromethylsulfonyl)imide (IL1-TFSI). Much improved cycling performance was achieved by using the functionalized ionic liquid IL1-TFSI.

What is claimed is:

1. An electrolyte comprising:
   a lithium salt; and
   an ionic liquid represented as a compound of Formula:

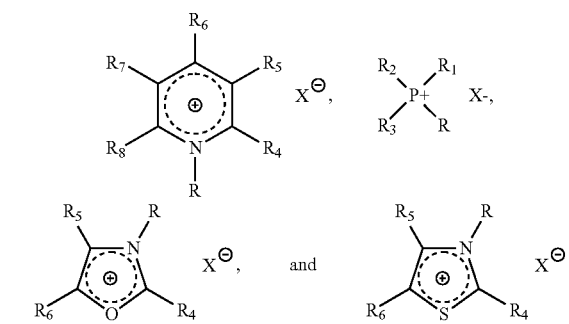

wherein
  R is selected from the group consisting of —$CH_2Si(R'')_2[OSi(R'')_2]_mO$—$Si(R'')_3$, —(R')—($OCH_2CH_2)_n$—(OR''), a $C_{3-5}$ cyclic carbonate, a sulfolane, an oxalic borate group, a maleic anhydride group, a succinic anhydride group, and a C$_{1-6}$ alkyl group substituted with a substituent selected from an isocyanate, sulfone, sulfolane, —OCO$_2$R", C$_{3-5}$ cyclic carbonate, or oxalic borate group;

R' is a C$_{1-4}$ alkylene group;

R" is an alkyl group;

R$_1$, R$_2$, and R$_3$ are independently at each occurrence an alkyl, haloalkyl, alkyl substituted with carboxylate, aminoalkyl, cycloalkyl, aryl, heteroaryl, aralkyl, or heteroaralkyl group; or two of R$_1$, R$_2$ and R$_3$ join together to form a C$_{4-5}$ alkylene group;

R$_4$, R$_5$, R$_6$, R$_7$, and R$_8$ are independently at each occurrence H or an alkyl, haloalkyl, hydroxyalkyl, cycloalkyl, aryl, heteroaryl, aralkyl, or heteroaralkyl group;

X$^-$ is an anion selected from the group consisting of boron tetrafluoride, aluminate, bis(oxalato)borate, difluoro(oxalate)borate, phosphorus hexafluoride, alkyl sulfonate, fluoroalkyl sulfonate, aryl sulfonate, bis(alkylsulfonyl)amide, perchlorate, bis(fluoroalkylsulfonyl)amide, bis(arylsulfonyl)amide, alkyl fluorophosphate, (fluoroalkylsulfonyl)(fluoroalkylcarbonyl)amide, halide, nitrate, nitrite, sulfate, hydrogen sulfate, alkyl sulfate, aryl sulfate, carbonate, bicarbonate, perfluoroalkyl group substituted with carboxylate, phosphate, hydrogen phosphate, dihydrogen phosphate, hypochlorite, an anionic site of a cation-exchange resin, and a mixture of any two or more thereof;

n is an integer from 1 to 4; and m is an integer from 0 to 10.

2. The electrolyte of claim 1, wherein the lithium salt is selected from the group consisting of Li[CF$_3$CO$_2$]; Li[C$_2$F$_5$CO$_2$]; Li[ClO$_4$]; Li[BF$_4$]; Li[AsF$_6$]; Li[PF$_6$]; Li[PF$_2$(C$_2$O$_4$)$_2$]; Li[PF$_4$C$_2$O$_4$]; Li[CF$_3$SO$_3$]; Li[N(CF$_3$SO$_2$)$_2$]; Li[C(CF$_3$SO$_2$)$_3$]; Li[N(SO$_2$C$_2$F$_5$)$_2$]; lithium alkyl fluorophosphates; Li[B(C$_2$O$_4$)$_2$]; Li[BF$_2$C$_2$O$_4$]; Li$_2$[B$_{12}$Z$_{12-j}$H$_j$]; Li$_2$[B$_{10}$Z$_{10-j'}$H$_{j'}$]; and a mixture of any two or more thereof, wherein Z is independently at each occurrence a halogen, j is an integer from 0 to 12 and j' is an integer from 1 to 10.

3. The electrolyte of claim 2 wherein the concentration of the lithium salt present in the ionic liquid is from about 0.01 M to about 1.5 M.

4. The electrolyte of claim 1 further comprising an aprotic solvent.

5. The electrolyte of claim 1 further comprising an aprotic gel polymer carrier/solvent.

6. The electrolyte of claim 1 further comprising an electrode stabilizing additive.

7. The electrolyte of claim 1, wherein the ionic liquid has the Formula selected from the group consisting of:

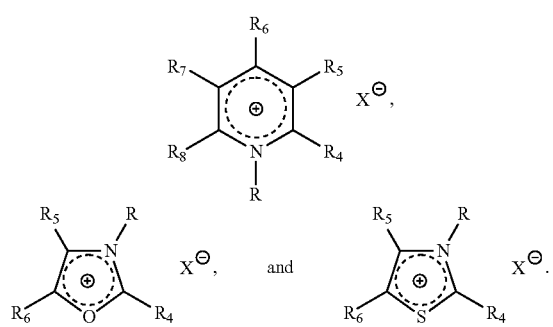

8. The electrolyte of claim 7, wherein R$_4$, R$_5$, R$_6$, R$_7$, and R$_8$ are independently at each occurrence a hydrogen or a C$_{1-6}$ alkyl group.

9. The electrolyte of claim 1 wherein the ionic liquid has the Formula:

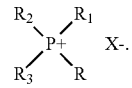

10. The electrolyte of claim 9, wherein R is selected from the group consisting of —(R')—(OCH$_2$CH$_2$)$_n$—(OR"), —CH$_2$Si(R")$_2$[OSi(R")$_2$]$_m$OSi(R")$_3$, and a C$_{1-6}$ alkyl group substituted with a sulfone group.

11. The electrolyte of claim 9, wherein R is —(CH$_2$)—(OCH$_2$CH$_2$)$_n$—(OCH$_3$), —CH$_2$Si(CH$_3$)$_2$[OSi(CH$_3$)$_2$]$_m$OSi(CH$_3$)$_3$, or —(CH$_2$)$_n$—SO$_2$CH$_3$.

12. The electrolyte of claim 9, wherein R$_1$, R$_2$, and R$_3$ are independently at each occurrence selected from the group consisting of a C$_{1-6}$ alkyl, hydroxyalkyl, and haloalkyl group.

13. The electrolyte of claim 1, wherein X$^-$ is [CF$_3$CO$_2$]$^-$; [C$_2$F$_5$CO$_2$]$^-$; [ClO$_4$]$^-$; ['BF$_4$]$^-$; [AsF$_6$]$^-$; [PF$_6$]$^-$; [PF$_2$(C$_2$O$_4$)$_2$]$^-$; [PF$_4$C$_2$O$_4$]$^-$; [CF$_3$SO$_3$]$^-$; [N(CF$_3$SO$_2$)$_2$]$^-$; [C(CF$_3$SO$_2$)$_3$]$^-$; [N(SO$_2$C$_2$F$_5$)$_2$]$^-$; alkyl fluorophosphate; [B(C$_2$O$_4$)$_2$]$^-$; [BF$_2$C$_2$O$_4$]$^-$; [B$_{12}$Y$_{12-k}$H$_k$]$^{2-}$; [B$_{10}$Y$_{10-k'}$H$_{k'}$]$^{2-}$; or a mixture of any two or more thereof, wherein Y is independently at each occurrence a halogen, k is an integer from 0 to 12 and k' is an integer from 1 to 10.

14. The electrolyte of claim 1, wherein the ionic liquid comprises:
- 1-ethyl-3-((2-methoxyethoxy)methyl)-1H-imidazol-3-ium bis(trifluoromethanesulfonyl)imide,
- 1-ethyl-3-((2-(2-methoxyethoxyl)ethoxy)methyl)-1H-imidazol-3-ium bis(trifluoromethanesulfonyl)imide,
- 3-2,5,8,11-tetraoxadodecyl-1-ethyl-1H-imidazol-3-ium bis(trifluoromethanesulfonyl)imide,
- 1-ethyl-3-((2-methoxyethoxy)methyl)-1H-imidazol-3-ium bis(fluoromethanesulfonyl)imide,
- 1-ethyl-3-((2-(2-methoxyethoxyl)ethoxy)methyl)-1H-imidazol-3-ium bis(fluoromethanesulfonyl)imide,
- 3-2,5,8,11-tetraoxadodecyl-1-ethyl-1H-imidazol-3-ium bis(fluoromethanesulfonyl)imide;
- 1-ethyl-3-((2-methoxyethoxy)methyl)-1H-imidazol-3-ium bis(oxalato)borate,
- 1-ethyl-3-((2-(2-methoxyethoxyl)ethoxy)methyl)-1H-imidazol-3-ium bis(oxalato)borate,
- 3-2,5,8,1-tetraoxadodecyl-1-ethyl-1H-imidazol-3-ium bis(oxalato)borate;
- 1-ethyl-3-((2-methoxyethoxy)methyl)-1H-imidazol-3-ium hexafluorophosphate,
- 1-ethyl-3-((2-(2-methoxyethoxyl)ethoxy)methyl)-1H-imidazol-3-ium hexafluorophosphate,
- 3-2,5,8,11-tetraoxadodecyl-1-ethyl-1H-imidazol-3-ium hexafluorophosphate,
- 1-ethyl-3-(methylenepentamethyldisiloxane)-1H-imidazol-3-ium bis(trifluoromethanesulfonyl)imide,
- 1-ethyl-3-(methyleneheptamethyltrisiloxane)-1H-imidazol-3-ium bis(trifluoromethanesulfonyl)imide,
- 1-ethyl-3-(methyleneoctamethyltetrasiloxane)-1H-imidazol-3-ium bis(trifluoromethanesulfonyl)imide,
- 1-ethyl-3-(methylenepentamethyldisiloxane)-1H-imidazol-3-ium bis(oxalato)borate,
- 1-ethyl-3-(methyleneheptamethyltrisiloxane)-1H-imidazol-3-ium bis(oxalato)borate, 1-ethyl-3-(methyleneoctamethyltetrasiloxane)-1H-imidazol-3-ium bis(oxalato)borate,
1-ethyl-3-(methylenepentamethyldisiloxane)-1H-imidazol-3-ium bis(fluoromethanesulfonyl)imide,
1-ethyl-3-(methyleneheptamethyltrisiloxane)-1H-imidazol-3-ium bis(fluoromethanesulfonyl)imide,
1-ethyl-3-(methyleneoctamethyltetrasiloxane)-1H-imidazol-3-ium bis(fluoromethanesulfonyl)imide;
1-ethyl-3-(methylenepentamethyldisiloxane)-1H-imidazol-3-ium hexafluorophosphate,
1-ethyl-3-(methyleneheptamethyltrisiloxane)-1H-imidazol-3-ium hexafluorophosphate,
1-ethyl-3-(methyleneoctamethyltetrasiloxane)-1H-imidazol-3-ium hexafluorophosphate,
1-ethyl-3-(2-(methylsulfonyl)ethyl)-1H-imidazol-3-ium bis(trifluoromethanesulfonyl)imide,
1-ethyl-3-(2-(ethylsulfonyl)ethyl)-1H-imidazol-3-ium bis(trifluoromethanesulfonyl)imide,
1-ethyl-3-(2-(propylsulfonyl)ethyl)-1H-imidazol-3-ium bis(trifluoromethanesulfonyl)imide,
1-ethyl-3-(2-(butylsulfonyl)ethyl)-1H-imidazol-3-ium bis(trifluoromethanesulfonyl)imide,
1-ethyl-3-(2-(methylsulfonyl)ethyl)-1H-imidazol-3-ium bis(oxalato)borate,
1-ethyl-3-(2-(ethylsulfonyl)ethyl)-1H-imidazol-3-ium bis(oxalato)borate,
1-ethyl-3-(2-(propylsulfonyl)ethyl)-1H-imidazol-3-ium bis(oxalato)borate,
1-ethyl-3-(2-(butylsulfonyl)ethyl)-1H-imidazol-3-ium bis(oxalato)borate,
1-ethyl-3-(2-(methylsulfonyl)ethyl)-1H-imidazol-3-ium bis(fluoromethanesulfonyl)imide,
1-ethyl-3-(2-(ethylsulfonyl)ethyl)-1H-imidazol-3-ium bis(fluoromethanesulfonyl)imide,
1-ethyl-3-(2-(propylsulfonyl)ethyl)-1H-imidazol-3-ium bis(fluoromethanesulfonyl)imide;
1-ethyl-3-(2-(butylsulfonyl)ethyl)-1H-imidazol-3-ium bis(fluoromethanesulfonyl)imide;
1-ethyl-3-(2-(methylsulfonyl)ethyl)-1H-imidazol-3-ium hexafluorophosphate,
1-ethyl-3-(2-(ethylsulfonyl)ethyl)-1H-imidazol-3-ium hexafluorophosphate,
1-ethyl-3-(2-(propylsulfonyl)ethyl)-1H-imidazol-3-ium hexafluorophosphate,
1-ethyl-3-(2-(butylsulfonyl)ethyl)-1H-imidazol-3-ium hexafluorophosphate
1-ethyl-3-((2-oxo-1,3-dioxolan-4-yl)methyl)-1H-imidazol-3-ium bis(trifluoromethanesulfonyl)imide,
1-ethyl-3-((2-oxo-1,3-dioxolan-4-yl)ethyl)-1H-imidazol-3-ium bis(trifluoromethanesulfonyl)imide,
1-ethyl-3-((2-oxo-1,3-dioxolan-4-yl)propyl)-1H-imidazol-3-ium bis(trifluoromethanesulfonyl)imide,
1-ethyl-3-((2-oxo-1,3-dioxolan-4-yl)methyl)-1H-imidazol-3-ium bis(oxalato)borate,
1-ethyl-3-((2-oxo-1,3-dioxolan-4-yl)ethyl)-1H-imidazol-3-ium bis(oxalato)borate,
1-ethyl-3-((2-oxo-1,3-dioxolan-4-yl)propyl)-1H-imidazol-3-ium bis(oxalato)borate,
1-ethyl-3-((2-oxo-1,3-dioxolan-4-yl)methyl)-1H-imidazol-3-ium bis(fluoromethanesulfonyl)imide,
1-ethyl-3-((2-oxo-1,3-dioxolan-4-yl)ethyl)-1H-imidazol-3-ium bis(fluoromethanesulfonyl)imide,
1-ethyl-3-((2-oxo-1,3-dioxolan-4-yl)propyl)-1H-imidazol-3-ium bis(fluoromethanesulfonyl)imide;
1-ethyl-3-((2-oxo-1,3-dioxolan-4-yl)methyl)-1H-imidazol-3-ium hexafluorophosphate,
1-ethyl-3-((2-oxo-1,3-dioxolan-4-yl)ethyl)-1H-imidazol-3-ium hexafluorophosphate, or
1-ethyl-3-((2-oxo-1,3-dioxolan-4-yl)propyl)-1H-imidazol-3-ium hexafluorophosphate.

15. An electrochemical device comprising a cathode; an anode; and an electrolyte comprising an ionic liquid of claim 14.

16. The electrolyte of claim 1, wherein the ionic liquid comprises:
triethyl((2-methoxyethoxy)methyl)phosphonium bis(trifluoromethylsulfonyl)imide,
triethyl((2-(2-methoxyethoxyl)ethoxy)methyl)phosphonium bis(trifluoromethylsulfonyl)imide,
triethyl((2-(2-(2-methoxyethoxyl)ethoxy)ethoxy)methyl)phosphonium bis(trifluoromethylsulfonyl)imide,
triethyl((2-methoxyethoxy)methyl)phosphonium bis(fluoromethylsulfonyl)imide,
triethyl((2-(2-methoxyethoxyl)ethoxy)methyl)phosphonium bis(fluoromethylsulfonyl)imide,
triethyl((2-(2-(2-methoxyethoxyl)ethoxy)ethoxy)methyl)phosphonium bis(fluoromethylsulfonyl)imide,
triethyl((2-methoxyethoxy)methyl)phosphonium bis(oxalato)borate,
triethyl((2-(2-methoxyethoxyl)ethoxy)methyl)phosphonium bis(oxalato)borate,
triethyl((2-(2-(2-methoxyethoxyl)ethoxy)ethoxy)methyl)phosphonium bis(oxalato)borate,
triethyl((2-methoxyethoxy)methyl)phosphonium hexafluorophosphate,
triethyl((2-(2-methoxyethoxyl)ethoxy)methyl)phosphonium hexafluorophosphate,
triethyl((2-(2-(2-methoxyethoxyl)ethoxy)ethoxy)methyl)phosphonium hexafluorophosphate,
triethyl-(methylenepentamethyldisiloxane)phosphonium bis(trifluoromethylsulfonyl)imide,
triethyl-(methyleneheptamethyltrisiloxane)phosphonium bis(trifluoromethylsulfonyl)imide,
triethyl-(methyleneoctamethyltetrasiloxane)phosphonium bis(trifluoromethylsulfonyl)imide,
triethyl-(methylenepentamethyldisiloxane)phosphonium bis(fluoromethylsulfonyl)imide,
triethyl-(methyleneheptamethyltrisiloxane)phosphonium bis(fluoromethylsulfonyl)imide,
triethyl-(methyleneoctamethyltetrasiloxane)phosphonium bis(fluoromethylsulfonyl)imide, triethyl-(methylenepentamethyldisiloxane)phosphonium bis(oxalato)borate,
triethyl-(methyleneheptamethyltrisiloxane)phosphonium bis(oxalato)borate,
triethyl-(methyleneoctamethyltetrasiloxane)phosphonium bis(oxalato)borate,
triethyl-(methylenepentamethyldisiloxane)phosphonium hexafluorophosphate,
triethyl-(methyleneheptamethyltrisiloxane)phosphonium hexafluorophosphate,
triethyl-(methyleneoctamethyltetrasiloxane)phosphonium hexafluorophosphate,
triethyl-(2-(methylsulfonyl)ethyl)phosphonium bis(trifluoromethylsulfonyl)imide,
triethyl-(2-(ethylsulfonyl)ethyl)phosphonium bis(trifluoromethylsulfonyl)imide,
triethyl-(2-(propylsulfonyl)ethyl)phosphonium bis(trifluoromethylsulfonyl)imide,
triethyl-(2-(butylsulfonyl)ethyl)phosphonium bis(trifluoromethylsulfonyl)imide,
triethyl-(2-(methylsulfonyl)ethyl)phosphonium bis(fluoromethylsulfonyl)imide, triethyl-(2-(ethylsulfonyl)ethyl)phosphonium bis(fluoromethylsulfonyl)imide,
triethyl-(2-(propylsulfonyl)ethyl)phosphonium bis(fluoromethylsulfonyl)imide,
triethyl-(2-(butylsulfonyl)ethyl)phosphonium bis(fluoromethylsulfonyl)imide,
triethyl-(2-(methylsulfonyl)ethyl)phosphonium bis(oxalato)borate,
triethyl-(2-(ethylsulfonyl)ethyl)phosphonium bis(oxalato)borate,
triethyl-(2-(propylsulfonyl)ethyl)phosphonium bis(oxalato)borate,
triethyl-(2-(butylsulfonyl)ethyl)phosphonium bis(oxalato)borate,
triethyl-(2-(methylsulfonyl)ethyl)phosphonium hexafluorophosphate,
triethyl-(2-(ethylsulfonyl)ethyl)phosphonium hexafluorophosphate,
triethyl-(2-(propylsulfonyl)ethyl)phosphonium hexafluorophosphate,
triethyl-(2-(butylsulfonyl)ethyl)phosphonium hexafluorophosphate,
triethyl-3-((2-oxo-1,3-dioxolan-4-yl)methyl)phosphonium bis(trifluoromethylsulfonyl)imide,
triethyl-3-((2-oxo-1,3-dioxolan-4-yl)ethyl)phosphonium bis(trifluoromethylsulfonyl)imide,
triethyl-3-((2-oxo-1,3-dioxolan-4-yl)propyl)phosphonium bis(trifluoromethylsulfonyl)imide,
triethyl-3-((2-oxo-1,3-dioxolan-4-yl)methyl)phosphonium bis(fluoromethylsulfonyl)imide,
triethyl-3-((2-oxo-1,3-dioxolan-4-yl)ethyl)phosphonium bis(fluoromethylsulfonyl)imide,
triethyl-3-((2-oxo-1,3-dioxolan-4-yl)propyl)phosphonium bis(fluoromethylsulfonyl)imide,
triethyl-3-((2-oxo-1,3-dioxolan-4-yl)methyl)phosphonium bis(oxalato)borate,
triethyl-3-((2-oxo-1,3-dioxolan-4-yl)ethyl)phosphonium bis(oxalato)borate,
triethyl-3-((2-oxo-1,3-dioxolan-4-yl)propyl)phosphonium bis(oxalato)borate,
triethyl-3-((2-oxo-1,3-dioxolan-4-yl)methyl)phosphonium hexafluorophosphate,
triethyl-3-((2-oxo-1,3-dioxolan-4-yl)ethyl)phosphonium hexafluorophosphate, or
triethyl-3-((2-oxo-1,3-dioxolan-4-yl)propyl)phosphonium hexafluorophosphate.

17. An electrochemical device comprising a cathode; an anode; and an electrolyte comprising an ionic liquid of claim 16.

18. An electrochemical device comprising a cathode; an anode; and an electrolyte comprising an ionic liquid of claim 1.

19. The electrochemical device of claim 18 that is a lithium secondary battery.

20. The electrochemical device of claim 19 wherein the secondary battery is a lithium battery, a lithium-ion battery, a lithium-sulfur battery, a lithium-air battery, a sodium ion battery, or a magnesium battery.

* * * * *